United States Patent
Satou et al.

(10) Patent No.: US 11,659,839 B2
(45) Date of Patent: May 30, 2023

(54) RESISTANCE INDUCING AGENT FOR PLANTS

(71) Applicants: PANAC CO., LTD., Tokyo (JP); NATIONAL INSTITUTE OF TECHNOLOGY AND EVALUATION, Tokyo (JP)

(72) Inventors: Gouki Satou, Tokyo (JP); Toshichika Ooki, Tokyo (JP); Masahiro Koide, Tokyo (JP); Hiroshi Sekiguchi, Tokyo (JP)

(73) Assignees: PANAC CO., LTD., Tokyo (JP); NATIONAL INSTITUTE OF TECHNOLOGY AND EVALUATION, Tokyo (JP)

( * ) Notice: Subject to any disclaimer, the term of this patent is extended or adjusted under 35 U.S.C. 154(b) by 193 days.

(21) Appl. No.: 16/977,466

(22) PCT Filed: Mar. 22, 2019

(86) PCT No.: PCT/JP2019/012056
§ 371 (c)(1),
(2) Date: Sep. 1, 2020

(87) PCT Pub. No.: WO2019/188773
PCT Pub. Date: Oct. 3, 2019

(65) Prior Publication Data
US 2021/0360935 A1    Nov. 25, 2021

(30) Foreign Application Priority Data
Mar. 30, 2018  (JP) .............................. JP2018-067567

(51) Int. Cl.
*A01N 65/03* (2009.01)
*C12N 1/12* (2006.01)
*C12R 1/89* (2006.01)

(52) U.S. Cl.
CPC ............... *A01N 65/03* (2013.01); *C12N 1/12* (2013.01); *C12N 1/125* (2021.05); *C12R 2001/89* (2021.05)

(58) Field of Classification Search
CPC .......... A01N 65/03; C12N 1/12; C12N 1/125; C12R 2001/89
See application file for complete search history.

(56) References Cited

U.S. PATENT DOCUMENTS

2017/0226509 A1    8/2017  Perata et al. ......... C12N 15/113

FOREIGN PATENT DOCUMENTS

JP    07048214 A  *  2/1995
JP    2013-124241 A    6/2013
(Continued)

OTHER PUBLICATIONS

Zhang et al., International Journal of Biological Macromolecules, 2019, 128:761-767. (Year: 2019).*

(Continued)

*Primary Examiner* — Allison M Fox
*Assistant Examiner* — Qing Xu
(74) *Attorney, Agent, or Firm* — Stein IP, LLC

(57) ABSTRACT

Provided is a component having plant defense activity. A PR1 gene expression activator containing a culture of a unicellular alga containing a green photosynthetic pigment as an active ingredient; A plant defense activator containing a culture of a unicellular alga containing a green photosynthetic pigment as an active ingredient; A plant disease preventive or ameliorating agent containing a culture of a unicellular alga containing a green photosynthetic pigment as an active ingredient; and a method of producing a plant defense activating component containing: cultivating a unicellular alga containing a green photosynthetic pigment (Continued)

under an aerobic condition to produce a culture containing an extracellular polysaccharide.

4 Claims, 1 Drawing Sheet

Specification includes a Sequence Listing.

(56) References Cited

FOREIGN PATENT DOCUMENTS

| | | |
|---|---|---|
| JP | 2017-197456 A | 11/2017 |
| WO | WO 2016/174646 A1 | 11/2016 |
| WO | WO 2017/044774 A1 | 3/2017 |
| WO | WO 2017/218896 A1 | 12/2017 |

OTHER PUBLICATIONS

Liu et al., Journal of Applied Phycology, 2000, 12: 301-307. (Year: 2000).*

Sophie Trouvelot et al., "Carbohydrates in plant immunity and plant protection: roles and potential application as foliar sprays", Nov. 4, 2014, pp. 1-14.

Imke Lang et al., "Fatty acid profiles and their distribution patterns in microalgae: a comprehensive analysis of more than 2000 strains from the SAG culture collection", 2011, pp. 1-16.

"Uronema confervicola partial 18s rRNA gene".

Extended European Search Report dated Feb. 9, 2022, issued by the European Patent Office in corresponding application EP 19775007.8-1111.

Master Dissertation; Culture, Polysaccharide extraction and RAPD analysis of three species *Porphyridium*.

Search Report issued to Chinese Application No. 2019800177426.

Sachiko Ono et al., Evaluation of the Use of the Tobacco PR-1a Promoter to Monitor Defense Gene Expression by the Luciferase Bioluminescence Reporter System, Biosci. Biotechnol. Biochem., 2011, pp. 1796-1800.

International Search Report dated Jun. 18, 2019, issued to International Application No. PCT/JP2019/012056.

Stadnik, Marciel J, et al., Tropical Plant Pathology, 2014, pp. 111-118, vol. 39(2).

Klarzynsky, Molecular Plant-Microbe Interactions, 2003, pp. 115-122, vol. 16, No. 2.

*Chlorococcum* sp. (NBRC 113206) printout, Mar. 29, 2018.

Chloroidium saccharophilum (Yama) (NBRC 113207) printout, Mar. 29, 2018.

Chloroidium saccharophilum (Kami) (NBRC 113807) printout, Feb. 25, 2019.

*Geminella* sp. (NBRC 113205) printout, Mar. 29, 2018.

*Uronema* sp. (NBRC 113204) printout, Mar. 29, 2018.

\* cited by examiner

RESISTANCE INDUCING AGENT FOR PLANTS

CROSS-REFERENCE TO RELATED APPLICATIONS

This application is a national stage of International Stage Application No. PCT/JP2019/012056, filed Mar. 22, 2019, which claims the benefit of Japanese Application No. 2018-067567, filed Mar. 30, 2018, in the Japanese Patent Office, the disclosures of which are incorporated herein by reference.

SEQUENCE LISTING

The instant application contains a Sequence Listing which has been submitted electronically in ASCII format and is hereby incorporated by reference in its entirety. Said ASCII copy, created on Nov. 16, 2020, is named 0442_1008_SEQUENCE_LISTING.txt and is 15,559 bytes in size.

TECHNICAL FIELD

The present technology relates to a PR1 gene expression activator, a plant defense activator, and a plant disease preventive or ameliorating agent.

BACKGROUND ART

Agricultural chemicals have been heavily used to reduce diseases caused by pathogenic germs and to improve the growth or harvest of crops, such as farm crops, and garden plants in agricultural fields. Reductions in the usage of agricultural chemicals, however, are required with concern over exposure to chemicals in use, environmental impacts, and residual agricultural chemicals caused by the use of agricultural chemicals.

Nowadays, insect-resistant and herbicide-tolerant breeds (Bt) by gene recombination are becoming increasingly common. Unfortunately, such approaches are limited to specific breeds. In addition, people have a leaning toward farm crops and garden plants that are non-genetically modified.

Plant defense activators are being developed to produce agricultural chemicals that meet such requirements. The plant defense activation is not an action that destroys pathogens, but activates the defensive mechanisms inherent in plants. Plants themselves can hold off pathogens through such activation. According to general knowledge, compounds having plant defense activation do not rely on insecticidal or bactericidal activity and thus the compounds usually have several advantages, such as low emergence rates of resistant bacteria, reduced usage, durability of response, and less effects on organisms other than target plants. Unlike breed improvements and genetically modified crops, the plant defensive activating compounds have high versatility that can be applied to plants of interest, for example, farm crops, garden plants at required sites during any time of need.

Known examples of the plant defensive activating compound include salicylic acid, probenazole, and validamycin A, which have already been in practical use and commercially available in the form of plant defense activators. When a plant to which these plant defense activators are applied senses the attack of pathogens to its systemic acquired resistance, the plant increases the concentration of salicylic acid, and then expresses a group of PR gene families through a transcriptional regulator NPR1. resulting in high resistance to pathogens. In other words, the plant defense activator triggers a group of PR gene families in the plant, and allows the overall plant to acquire resistance to pathogens.

Methods of screening novel plant defense activators have also been developed using an expression monitoring system of a PR-1a gene based on a SAR model.

For example, PL 1 discloses that heterocyclic compounds having halogen and oxo groups exhibit enhancements of the PR-1a gene expression activity and that such enhancements can induce or facilitate expression of a PR protein having broad antibiotic spectrum and can produce plant defense activation.

CITATION LIST

Patent Literature

PL 1: Japanese Unexamined Patent Application Publication No. 2013-124241

PL 2: Japanese Unexamined Patent Application Publication No. 2017-197456

Non Patent Literature

NPL 1: Evaluation of the Use of the Tobacco PR-1a Promoter to Monitor Defense Gene Expression by the Luciferase Bioluminescence Reporter System, Biosci. Biotechnol. Biochem, 75(9), 1796-1800 (2011).

SUMMARY OF INVENTION

Technical Problem

Unfortunately, scientific knowledge on research and development of plant defense activators are still insufficient; hence, a variety of investigations have been carried out on components having plant defensive activity. The present inventors believe such components, which enhance the resistance of plants, have reduced disadvantages causing growth inhibition of the plants.

It is a primary object of the present technology to provide a component having a plant defensive activity.

Solution to Problem

The present inventors have found a compound that exhibits PR1 gene expression activity involving plant defensive induction through PR-1a gene expression activation tests.

The present inventor, as a result of extensive studies, has found that a culture of a unicellular alga containing a green photosynthetic pigment contains an extracellular polysaccharide and has PR1 gene expression activity and plant defense activity, and has completed the present invention. The present invention accordingly provides the following aspects:

Aspect 1. A PR1 gene expression activator containing a culture of a unicellular alga containing a green photosynthetic pigment as an active ingredient.

Aspect 2. The PR1 gene expression activator according to Aspect 1, wherein the unicellular alga is an alga of class Trebouxiophyceae and/or an alga of class Chlorophyceae.

Aspect 3. The PR1 gene expression activator according to Aspect 1 or 2, wherein the unicellular alga is at least one selected from the group consisting of genera *Geminella, Uronema, Chlorococcum*, and *Chloroidium*.

Aspect 4. The PR1 gene expression activator according to any one of Aspects 1 to 3, wherein the culture contains an extracellular polysaccharide containing uronic acid.

Aspect 5. The PR1 gene expression activator according to any one of Aspects 1 to 4, wherein the culture contains an extracellular polysaccharide containing 5 to 40 mass % uronic acid and at least one neutral monosaccharide selected from the group consisting of mannose, galactose, and rhamnose.

Aspect 6. The PR1 gene expression activator according to any one of Aspects 1 to 5, wherein the unicellular alga contains at least one selected from the group consisting of [1] Chlorophyceae *Uronema* sp. (NBRC 113204) strain; [2] Trebouxiophyceae *Geminella* sp. (NBRC 113205) strain; [3] Chlorophyceae *Chlorococcum* sp. (NBRC 113206) strain; [4]Trebouxiophyceae *Chloroidium saccharophilum* YAMA (NBRC 113207) strain; and [5] Trebouxiophyceae *Chloroidium saccharophilum* KAMI (NBRC 113807) strain.

Aspect 7. A plant defense activator containing a culture of a unicellular alga containing a green photosynthetic pigment as an active ingredient.

Aspect 8. A plant disease preventive or ameliorating agent containing a culture of a unicellular alga containing a green photosynthetic pigment as an active ingredient.

Aspect 9. A method of producing a plant defense activating component containing: cultivating a unicellular alga containing a green photosynthetic pigment under an aerobic condition to produce a culture containing an extracellular polysaccharide.

Aspect 10. Use of a unicellular alga containing a green photosynthetic pigment in production of a plant defense activating component.

Advantageous Effects

The present technology provides a component having plant defensive activity. The advantageous effects described herein are not definitive and may be any effect described in the specification.

DESCRIPTION OF EMBODIMENTS

Figure 1:
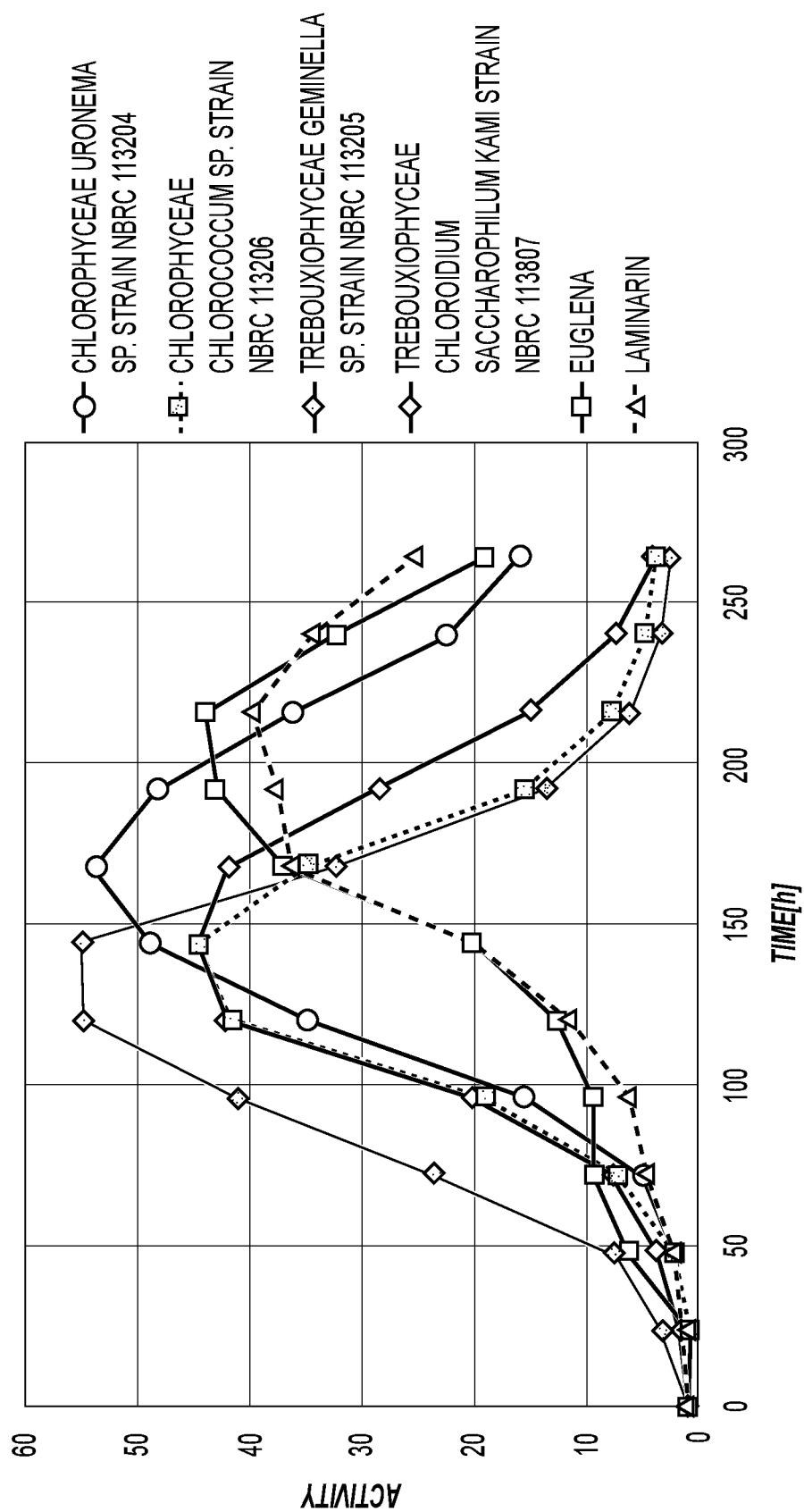
FIG. 1 shows a chronological change in activation level of each of cultures of algae, laminarin (positive control), and a control ($H_2O$).

Preferred embodiments of the present technology will now be described. The present technology should not be limited to the preferred embodiment and thus can be modified without limitation within the technical scope. It is noted that the percentage throughout the specification is on a mass basis unless otherwise stated.

1. Culture of Green Alga and Method of Producing the Culture

The present technology relates to a PR1 gene expression activator, a plant defense activator, and a plant disease preventive or ameliorating agent that contain a culture of a unicellular alga containing a green photosynthetic pigment as an active ingredient.

The culture of the technology has PR1 gene expression activity, plant defensive activity, and plant disease protection activity, as will be described below. The culture should preferably contain extracellularly produced polysaccharide.

The culture of the unicellular alga containing a green photosynthetic pigment of the present technology (also referred to as "unicellular green alga") may be produced with a green alga by the following nonlimiting method.

Throughout the specification, the term "alga containing a green photosynthetic pigment" refers to an alga that has a green appearance in broad sense and contains chlorophylls a and b as photosynthetic pigments. The alga may also contain any other chlorophyll or pigment. The unicellular algae may be present not only in a discrete state but also a gregarious state.

Nonlimiting examples of the unicellular green alga usable in the present technology include algae of classes Chlorophyceae and Trebouxiophyceae. These algae may be used alone or in combination of two or more.

The unicellular green alga usable in the present technology may include one or two or more selected from the group consisting of *Euglena, Chlorella, Uronema, Chlorococcum, Geminella*, and *Chloroidium*. Among these preferred are one or two or more selected from the group consisting of genera *Geminella, Uronema, Chlorococcum*, and *Chloroidium*. Examples of the alga strain include alga strains contained in commercially-available products; alga strains preserved in the form of culture collection in microorganism preservation organizations, such as NITE Biological Resource Center (NBRC) Culture Collection, American Type Culture Collection (ATCC); alga strains preserved in the form of deposited strains preserved in international deposition organizations, such as National Institute of Technology and Evaluation (NITE); and alga strains that will be discovered in future. Alga strains that can produce cultures achieving the purpose of the present technology, i.e., activation of PR1 genes can be selected.

For example, the following alga strains [1] to [5] are available from the culture collection of the NITE Biological Resource Center (NBRC) (www.nbrc.nite.go.jp, 2-5-8 Kazusakamatar, Kisarazu-shi, Chiba 2920818, Japan). These may be used alone or in combination of two or more.
[1] Chlorophyceae *Uronema* sp. (NBRC 113204) alga strain (www.nbrc.nite.go.jp)/published on 2018 Mar. 29;
[2] Trebouxiophyceae *Geminella* sp. (NBRC 113205) alga strain (www.nbrc.nite.go.jp)/published on 2018 Mar. 29;
[3] Chlorophyceae *Chlorococcum* sp. (NBRC 113206) alga strain (www.nbrc.nite.go.jp, 2-5-8 Kazusakamatari. Kisarazu-shi, Chiba 2920818, Japan) deposited 2018/accepted 2018/01126/published on 2018 Mar. 29;
[4] Trebouxiophyceae *Chloroidium saccharophilum* YAMA (NBRC 113207) (YAMA-Mizu-03-3) alga strain (www.nbrc.nite.go.jp)/published on 2018 Mar. 29; and
[5] Trebouxiophyceae *Chloroidium saccharophilum* KAMI (NBRC 113807) (KAMI-04 (3)) alga strain (www.nbrc.nite.go.jp)/published on 2019 Feb. 25.

It should be noted that the URL of the home page of the NITE Biological Resource Center (NBRC) was changed from "www.nbrc.nite.go.jp (* indicates NBRC No.) to "www.nite.go.jp" in March, 2019.

Examples of the alga of class Chlorophyceae include Chlorophyceae *Uronema* and Chlorophyceae *Chlorococcum*.

Examples of the alga of class Trebouxiophyceae include. Trebouxiophyceae *Geminella* and Trebouxiophyceae *Chloroidium*.

Preferred *Chloroidium* that can achieve the advantageous effects of the present technology contains algae of genus *Chloroidium*. A preferred alga of genus *Chloroidium* is Trebouxiophyceae *Chloroidium saccharophilum* (NBRC 113207).

Preferred *Euglena* that can achieve the advantageous effects of the present technology contains algae of genus *Euglena*. A preferred alga of genus *Euglena* is *Euglena gracilis*.

Preferred *Chlorella* that can achieve the advantageous effects of the present technology contains algae of genus *Chlorella*. A preferred alga of genus *Chlorella* is *Chlorella vulgaris*, in particular, *Chlorella vulgaris* Chikugo strain (available from *Chlorella* Industry Col, Ltd.).

Preferred *Uronema* that can achieve the advantageous effects of the present technology contains algae of genus *Uronema*. A preferred alga of genus *Uronema* is Chlorophyceae *Uronema* sp. (NBRC 113204).

Preferred *Chlorococcum* that can achieve the advantageous effects of the present technology contains algae of genus *Chlorococcum*. A preferred alga of genus *Chlorococcum* is Chlorophyceae *Chlorococcum* sp. (NBRC 113206).

Preferred *Geminella* that can achieve the advantageous effects of the present technology contains algae of genus *Geminella*. A preferred alga of genus *Geminella* is Trebouxiophyceae *Geminella* sp. (NBRC 113205).

Preferred *Chloroidium* that can achieve the advantageous effects of the present technology contains algae of genus *Chloroidium*. A preferred alga of genus *Chloroidium* includes Trebouxiophyceae *Chloroidium saccharophilum* YAMA (NBRC 113207) (YAMA-Mizu-03-3) (hereinafter, also referred to as YAMA) and Trebouxiophyceae *Chloroidium saccharophilum* KAMI (NBRC 113807) (KAMI-04-(3)) (hereinafter, KAMI). Trebouxiophyceae *Chloroidium saccharophilum* KAMI (NBRC 113807), which has high productivity, is more preferred.

In the present technology, alga strains that are substantially homogeneous with the alga strains described above can also be available. The term "substantially homogeneous alga strain" indicates at least 99.5% (preferably at least 99.8%, more preferably 100%) identity of the base sequence (for example, SEQ ID NOs: 1 to 5) of the 18SrRNA gene and the same algological properties (by morphological observation and on production of extracellular polysaccharide) in comparison with the alga strains descried above. The alga strains and substantially homogeneous alga strains of the present technology may be bred after mutation, gene recombination, selection of natural mutation strains that have the same advantageous effects, in particular productivity of PR1 gene activating components, of the present technology.

The unicellular green alga of the present technology is preferably incubated using a basic culture medium used for culture of general unicellular algae.

The basic culture medium used for culture of general unicellular algae contains, for example, trace amounts of inorganic salts, such as $KH_2PO_4$ and $MgSO_4$, and nitrogen sources, such as ammonium sulfate and urea. The deviation of the content of each component in the basic culture medium preferably lies within ±10%.

Examples of the preferred basic culture medium include an AF6 culture medium, a BG11 culture medium, and a KO2 culture medium, as will be described below in Examples. Among them, the AF6 culture medium is suitable for *Chlorella, Chlorococcum, Geminella, Chloroidium*, and *Euglena*. The BG11 culture medium is suitable for *Uronema* and *Chloroidium*. The KO2 culture medium is suitable for *Euglena*.

In order to ensure stable production of the culture containing the polysaccharide of the present technology, aerobic cultivation is preferred. Particularly preferred is aeration cultivation that can improve the productivity of the polysaccharide. Examples of the aeration means include agitation, shaking, air blow, and bubbling. These means may be carried out alone or in combination of two or more. Moderate gas can thereby be incorporated into the culture medium during cultivation.

The cultivation may be carried out at any temperature, usually at normal temperature in the range of 5 to 40° C.

The pH (20° C.) of the culture medium preferably lies at the pH ±2, preferably pH ±1 of the culture medium composition. The pH of the culture medium is preferably in the range of 1.5 to 9.5. The pH of the culture medium is more preferably in the range of 6 to 9 for cultivation of *Uronema, Chlorococcum, Geminella, Chloroidium*, and *Chlorella*. One cycle of cultivation term is preferably in the range of four days to about three weeks, more preferably seven days to two weeks, for stable production of the polysaccharide, although the term may be modified.

The cultivation may be carried out under any illuminance. The preferred illuminance that can readily produce a culture containing polysaccharide ranges from 1500 lux to 10000 lux.

In the case of incubation of a large number of algae cells under autotrophic cultivation conditions, solar light and artificial light from lamps for cultivating plants and LEDs can be used, preferably with supply of carbon dioxide gas and agitation of the medium.

In the present technology, the culture containing polysaccharide can be produced with unicellular green algae, preferably *Chlorella, Chlorococcum, Geminella, Euglena, Uronema*, and *Chloroidium* by autotrophic cultivation, which is an advantage of the present technology.

Besides autotrophic cultivation, the culture containing polysaccharide of the present technology may be produced in a basic medium that is suitable for cultivation of usual unicellular algae culture medium and contains carbon sources, such as glucose. The culture medium may also contain nitrogen sources and phosphorus sources, in addition to the carbon sources. Alternatively, the culture medium used in the present technology may be swage water or digestive fluid or liquid fertilizer that is generated in methane fermenters.

The culture in the present technology may be produced by either a batch process or a continuous process. A continuous process is preferred for improved productivity. The cultivation may be in an open system, such as an open-air cultivation tank, or a closed system, such as a closed cultivation tank. Preferred is cultivation in a closed system the operation conditions of which can be readily controlled.

It is preferred that the culture containing polysaccharide of the present technology produced using the unicellular green alga be separated from the alga cells by physical means, such as washing with aqueous solution, ultrasonic application, centrifugal separation, or filtration, or by chemical means. Supernatant containing polysaccharide can thereby be prepared.

Since it is speculated that the extracellular metabolites of algae contribute to the advantageous effect of the present technology, the culture may contain not only polysaccharide, but also metabolites from algae, such as proteins, peptides, amino acids, nucleic acids, organic acids and lipids.

Since extracellular metabolites of algae can be used as a culture of the present technology, the culture can be continuously prepared while polysaccharide is separated from the surface of the alga cells. Thus, the algae of the present technology are superior in view of continuous cultivation. In continuous preparation of the culture, centrifugal separation (preferably at 5000 to 9000 rpm, for about five minutes) and filtration (for example, filtration auxiliary agent and filter) may be used alone or in combination of two or more.

The resulting culture may be processed into diluted solution, concentrated solution, or dried matter as needed. Means for drying is preferably lyophilization.

The culture of the present technology preferably contains at least polysaccharide. The polysaccharide may be bonded to any other substance, for example, protein, peptide, amino acid, nucleic acid, organic acid, or lipid within the scope of the advantageous effects of the present technology. Examples of the polysaccharide include glycoproteins, peptide glycans, and glycolipids.

The yield of the polysaccharide in the broth in the present technology is at least 20 mg/L, preferably at least 50 mg/L, more preferably at least 100 mg/L. In the present technology, the yield can be increased to 300 to 500 mg/L.

Preferred algae that can produce polysaccharide at high efficiency are *Chlorococcum* and *Chloroidium*. Preferred algae that can produce polysaccharide having high advantageous effects are *Chlorococcum* and *Uronema*.

The culture of algae in the present technology preferably contains at least 20 mass % polysaccharide on the basis of dry state, more preferably at least 20 mass % neutral monosaccharide.

The polysaccharide in the culture of algae preferably contains at least 5 mass %. more preferably at least 10 mass % uronic acid. The upper limit of the uronic acid content is preferably 40 mass %, more preferably 35 mass %, further preferably 30 mass %, most preferably 25 mass %. Accordingly, the uronic acid content preferably ranges from 5 to 30 mass %. Among polysaccharides preferred are extracellular polysaccharides that can be readily recovered at a high yield.

The polysaccharides produced by unicellular green algae (preferably algae of class Chlorophyceae and/or algae of class Trebouxiophyceae) in the present technology preferably contain at least uronic acids as monosaccharide constituents. Preferred uronic acid is glucuronic acid. The advantageous effects, such as PR1 gene activation (as will be described below), of the present technology can thereby be achieved.

Neutral monosaccharide units contained in the polysaccharides in the present technology preferably contain hexasaccharides preferably aldohexose. More specifically. the neutral monosaccharide as a primary constituent preferably contains at least one of mannose, galactose, and rhamnose in view of advantageous effects of the present technology. The neutral monosaccharide more preferably contains mannose or rhamnose in view of advantageous effects of the present technology.

The extracellular polysaccharide in the culture of the present technology preferably contains uronic acid, more preferably contains uronic acid and neutral monosaccharide as monosaccharide constituents. The advantageous effects, such as PR1 gene activation (will be described below of the present technology can thereby be achieved. Preferred neutral monosaccharide contains one or two or more selected from the group consisting of mannose, galactose, and rhamnose.

Preferred are polysaccharide contained in a culture produced by at least one alga selected from the group consisting of *Uronema, Chlorococcum, Geminella* and *Chloroidium* algae that can achieve advantageous effects of the present technology.

The yield of polysaccharide produced by *Uronema* in a broth is preferably at least 20 mg/L.

The extracellular polysaccharide produced by *Uronema* hereinafter, also referred to as "*Uronema* polysaccharide") preferably contain uronic acid. The lower limit of the uronic acid content is preferably 5 mass %, more preferably 10 mass %, most preferably 15 mass %. The upper limit of the uronic acid content is preferably 35 mass %, more preferably 30 mass %. Accordingly, the uronic acid content preferably ranges from 10 to 30 mass %. The *Uronema* polysaccharide preferably contains glucuronic acid. The lower limit of the glucuronic acid content is preferably 5 mass %, more preferably 10 mass %, whereas the upper limit thereof is preferably 30 mass %, more preferably 20 mass %. Accordingly, the glucuronic acid content preferably ranges from 5 to 15 mass %, more preferably 10 to 15 mass %.

The neutral monosaccharide content in the polysaccharide produced by *Uronema* is preferably at least 20 mass %, and the neutral monosaccharide preferably contains at most 70 mass % other components.

Preferably the culture of *Uronema* contains 0 to 4 mass % mannose, 0 to 1.5 mass % arabinose, 0 to 1.5 mass % galactose, 0 to 2 mass % xylose, 0 to 6 mass % glucose, 5 to 20 mass % (more preferably 5 to 15 mass %) rhamnose, 0 to 1 mass % ribose, 0 to 1 mass % fucose, and 15 to 30 mass % uronic acid, alone or in combination of two or more.

The extracellular polysaccharide produced by *Uronema* preferably contains mannose and/or rhamnose as neutral saccharide, more preferably contains rhamnose as a primary component.

The proportion of the primary monosaccharides, mannose (Man), rhamnose (Rha), and glucose (Glc) in the neutral saccharides in the *Uronema* polysaccharide is preferably Man:Rha:Glc=1-10:5-20:1-10, more preferably Man:Rha:Glc=0-1:1-3:0-1. The ratio of Man:Rha in the primary monosaccharides in the *Uronema* polysaccharide is preferably 1-[1/3]:1.

The ratio of Rha:uronic acid (UA) in the primary monosaccharides in the *Uronema* polysaccharide is preferably 1-4:1-6, more preferably 1-2:1-3.

The preferred yield of the polysaccharide produced by *Chlorococcum* in the broth is at least 50 mg/L.

It is preferred that the extracellular polysaccharide produced by *Chlorococcum* (hereinafter, also referred to as "*Chlorococcum* polysaccharide") contain uronic acid. The lower limit of the uronic acid content is preferably 5 mass %, more preferably 10 mass %, whereas the upper limit thereof is preferably 25 mass %, more preferably 20 mass %. The uronic acid content accordingly ranges more preferably from 10 to 20 mass %. More preferably, the *Chlorococcum* polysaccharide contains glucuronic acid. The lower limit of the glucuronic acid content is preferably 5 mass %, more preferably 10 mass %, whereas the upper limit thereof is preferably 25 mass %, more preferably 20 mass %. The glucuronic acid content accordingly ranges more preferably from 10 to 20 mass %.

The polysaccharide produced by *Chlorococcum* contain preferably at least 60 mass %, more preferably at least 70 mass % neutral monosaccharide and at most 30 mass % other components.

In detail, the culture of *Chlorococcum* contain preferably 10 to 30 mass %, more preferably 14 to 25 mass % mannose, 10 to 30 mass %, more preferably 20 to 30 mass % arabinose, 10 to 30 mass %, more preferably 17 to 30 mass % galactose, 0 to 5 mass % xylose, 0 to 1 mass % glucose, 0 to 2 mass % rhamnose, 0 to 1 mass % ribose, 0 to 1 mass % fucose, and 10 to 20 mass % uronic acid, alone or in combination of two or more.

The extracellular polysaccharide produced by *Chlorococcum* preferably contains mannose, arabinose, and galactose as neutral saccharides. More preferably mannose, arabinose, and galactose are primary components.

The proportion of the primary monosaccharides in the neutral saccharide in the *Chlorococcum* polysaccharide is mannose (Man):arabinose (Ara):galactose (Gal)=preferably 1-3:1-3:1-3, more preferably 1-2:1-2:1-2. The proportion of the primary monosaccharides in the neutral saccharide in the *Chlorococcum* polysaccharide is preferably Man:Ara:Gal=1:1-2:1-2.

The proportion of the primary monosaccharides in the neutral saccharide in the *Chlorococcum* polysaccharide is preferably mannose (Man):arabinose (Ara):galactose (Gal):uronic acid (UA)=1-3:1-3:1-3:1-3, more preferably Man:Ara:Gal:UA=1-2:1-2:1-2:1-2.

The preferred yield of the polysaccharide produced by *Geminella* in the culture solution is at least 20 mg/L.

It is preferred that the extracellular polysaccharide produced by *Geminella* (hereinafter, also referred to as "*Geminella* polysaccharide") contain uronic acid. The lower limit of the uronic acid content is preferably 5 mass %, whereas the upper limit thereof is preferably 20 mass %. The uronic acid content accordingly ranges more preferably from 5 to 15 mass %. More preferably, the *Geminella* polysaccharide contains glucuronic acid. The lower limit of the glucuronic acid content is preferably 5 mass %, whereas the upper limit thereof is preferably 20 mass %, more preferably 15 mass %. The glucuronic acid content accordingly ranges more preferably from 5 to 15 mass %. The polysaccharide produced by *Geminella* preferably contains at least 35 mass %, more preferably at least 40 mass % neutral monosaccharide and at most 60 mass % other components.

The culture of *Geminella* preferably contains 0 to 30 mass %, more preferably 9 to 25 mass % mannose, 0 to 8 mass % arabinose, 3 to 20 mass % galactose, 0 to 3 mass % xylose, 0 to 1 mass % glucose, 2 to 20 mass % rhamnose, 0 to 1 mass % ribose, 0 to 4 mass % fucose, and 5 to 1 5 mass % uronic acid.

The neutral saccharide in the extracellular polysaccharide produced by *Geminella* contains primarily of mannose, galactose, and rhamnose.

The proportion of the primary monosaccharides in the neutral saccharide in the *Geminella* oligosaccharide is preferably mannose (Man):arabinose (Ara):galactose (Gal):rhamnose (Rha)=1-6:0-1:1-3:1-3, more preferably Man:Gal:Rha=1-6:1-2:1-2. In addition, the proportion of the primary monosaccharides in the neutral saccharide in the *Geminella* polysaccharide is preferably Man:Gal:Rha=1:0-[2/5]:0-[3/10]. More preferably the primary monosaccharide consists substantially of Man.

The proportion of the primary monosaccharides in the *Geminella* polysaccharide is preferably mannose (Man):galactose (Gal):rhamnose (Rha):uronic acid (UA)=1-6:0-1:1-3:1-3:1-4, more preferably Man:UA=1-2:1-2.

The yield of the polysaccharide produced by *Chloroidium* in the culture solution is preferably at least 250 mg/L.

The extracellular polysaccharide produced by *Chloroidium* (hereinafter, also referred to as "*Chloroidium* polysaccharide") preferably contains uronic acid. The lower limit of the uronic acid content is preferably 5 mass %, more preferably 10 mass %, whereas the upper limit thereof is preferably 30 mass %, more preferably 25 mass %. The uronic acid content accordingly ranges more preferably from 10 to 25 mass %. The *Chloroidium* polysaccharide more preferably contains glucuronic acid. The lower limit of the glucuronic acid is preferably 5 mass %, more preferably 10 mass %, whereas the upper limit thereof is preferably 25 mass %, more preferably 20 mass %. The glucuronic acid content accordingly ranges preferably from 5 to 15 mass %, more preferably 10 to 15 mass %.

The polysaccharide produced by *Chloroidium* preferably contains at least 30 mass %, more preferably at least 34 mass % neutral monosaccharide and at most 70 mass % other components.

The culture of *Chloroidium* preferably contains 3 to 18 mass % mannose, 3 to 12 mass % arabinose, 0 to 20 mass %, more preferably 5 to 15 mass % galactose, 0 to 9 mass % xylose, 0 to 5 mass % glucose, 0 to 5 mass % rhamnose, 0 to 1 mass % ribose, 0 to 1 mass % fucose, and 10 to 30 mass %, more preferably 15 to 25 mass % uronic acid.

The extracellular polysaccharide in the *Chloroidium* product preferably contains neutral saccharides containing primarily of mannose, arabinose, galactose, glucose, and xylose.

The proportion of the primary neutral saccharides in the *Chloroidium* polysaccharide is mannose (Man):arabinose (Ara):galactose (Gal):glucose (Glc):xylose (Xyl)=1-2:1-2:1-3:0-1:0-1.

The proportion of the main monosaccharides in the *Chloroidium* polysaccharide is preferably mannose (Man):arabinose (Ara):galactose (Gal):xylose (Xyl):glucose (Glc):uronic acid (UA)=1-2:0-2:1-3:0-1:0-1:1-4. The proportion of the main monosaccharides in the *Chloroidium* polysaccharide is preferably Man:Ara:Gal:Xyl:UA=1-2:0-1:1-2:0-1:1-3.

The proportion of the primary monosaccharides in the neutral saccharides in the polysaccharide of the *Chloroidium* KAMI alga (hereinafter also referred to as "*Chloroidium* KAMI polysaccharide") is preferably Man:Ara:Gal:Xyl:Rha=1-2:1-2:1-2:1-2:0-1. The uronic acid content in the *Chloroidium* KAMI polysaccharide ranges preferably from 5 to 30 mass %, more preferably from 10 to 30 mass %, and the glucuronic acid content preferably ranges from 5 to 15 mass %.

The proportion of the primary monosaccharides in the *Chloroidium* KAMI polysaccharide is Man:Ara:Gal:Xyl:Rha:UA=1-4:1-2:1-2:1-2:0-1:1-5.

The proportion of the primary monosaccharides in the neutral saccharide in the polysaccharide of the *Chloroidium* YAMA alga (hereinafter also referred to as "*Chloroidium* YAMA polysaccharide") is preferably Man:Gal:Glc=1-2:1-2:1. The uronic acid content in the *Chloroidium* YAMA polysaccharide preferably ranges from 10 to 20 mass %.

The proportion of the primary monosaccharides in the *Chloroidium* YAMA polysaccharide is preferably Man:Gal:Glc:UA=1-2:1-2:0-1:1-3, more preferably Man:Gal:UA=1-2:1-2:1-3.

The culture of the present technology may be purified by any known separation and refinement techniques, such as liquid-liquid separation, solid-liquid separation, membrane filtration, activated charcoal adsorption, resin adsorption, and/or ion exchanging, to remove impurities.

Polysaccharide may be recovered from the culture of the present technology by any known process for separation of the polysaccharide. For exemplary recovery of the water-soluble polysaccharide, the culture is dissolved in water, and then insoluble matter is removed to recover aqueous solution. The temperature of water is preferably kept at 5 to 40° C. The resulting solution is preferably allowed the stand for, for example, 5 to 15 hours at low temperature, for example, 1 to 10° C. The insoluble matter is preferably removed by physical means, such as centrifugal separation and/or ultrafiltration. High-purity polysaccharide having high solubility to water can thereby be prepared and used in a variety of applications.

2. Application of Culture of the Present Technology

Since the culture of the present technology has PR1 gene expression induction activity as described in Examples below, it can induce or promotes the expression of pathogenesis-related proteins (PR proteins), for example. The PR proteins are a general term indicating proteins that have antimicrobial activity or can produce antimicrobial substances. Since PR proteins generated by plants have significantly broad antibiotic spectra, the culture of the present technology is probably effective as antimicrobial agents against pathogenic microorganisms, such as filamentous fungi (for example, genus *Colletotrichum*), bacteria (for example, genus *Pseudomonas*), and viruses.

The culture of the present technology can induce the plant defensive activity by artificially switching on the PR-1a gene, which is one of the plant genes involved in tolerance to environmental stress. The culture of the present technology can thereby elicit stress tolerance inherent in plants. Examples of the cause of stress include conditions or diseases, such as inflammation and infection; and environments, such as temperature, dry weather, light, nutrients, concentrations of salts, and drugs. Examples of the stress tolerance include (1) resistance to diseases, such as promotion of hypersensitive cell death, promotion of production of antibacterial substances, and improvement in cell wall effects and (2) environmental durability, such as control of stomatal opening and closing and promotion of root elongation.

If a secondary stimulation such as salicylic acid is applied during induction of PR-1a gene promoter expression, rapid and strong induction activation are sometimes found. Such induction is probably caused by induction by secondary stimulation of salicylic acid (SA) signal transduction pathway that can induce the PR-1a gene expression. Since the culture of the present technology contributes to expression without secondary stimulation, it is believed that the defense response gene is highly pre-expressed to enhance the resistance of the plant. Plants can thereby have high resistance; hence, the culture of the present technology can be applied to prevention of disease or onset by pathogen infection.

Since the culture of the present technology has PR-1a gene expression induction activity, the present technology can rapidly respond to plants infected with pathogens and can be applied to therapy after developing the disease through appropriate adjustment of regimen and usage, for example, time of addition and amount of added culture.

The culture of the present technology, which has PR1 gene expression induction activation, accordingly has plant defense activity and plant disease preventive effects.

The culture of the present technology can be used as active ingredients in, for example. PR1 gene expression activators, plant defense activators, and plant disease preventive or ameliorating agents. The culture of the present technology can be used for achieving these activities. The culture of the present technology can also be used as a component of a preparation or composition, or used for production of a preparation or composition.

The culture of the present technology may be used in combination of two or more with any other ingredient depending on the purpose. Preferred are ingredients that can enhance the advantageous effects of the present technology.

Examples of the enhancer of the present technology include extracts derived from sea algae and microorganisms. Among these extracts preferred are extracts containing polysaccharides. The extracts can be prepared by known processes that include cultivation, sampling, and extraction.

Examples of sea algae include brown algae, such as *Sargassum thunbergii* (umitoranoo), sea tangle, *Hizikia fusiforme* (hijiki), *Fucus vesiculosus* (hibamata), *Sargassum enerve* (hondawara), *Tinocladia crassa* (mozuku), *Turbinaria ornata* (rappamoku), and *Undaria pinnatifida* (wakame); red algae, such as *Porphyra kuniedae* (asakusanori) and *Gelidium crinale* (tengusa); and green algae, such as sea lettuce (aosa), *Enteromorpha compressa* (aonori), *Acetabularia ryukyuensis* (kasanori), *Halimeda opuntia* (sabotengusa), *Caulerpa okamurae* (fusaiwazuta), and *Codium fragile* (miru).

Examples of the microorganism include fungi such as mushroom, bacteria, and molds such as rice malt.

These microorganisms may be used alone or in combination of two or more.

Among them, preferred are extracts derived from sea tangle, especially laminarin, which has slow-acting PR1 gene expression induction activity. A combination of slow-acting laminarin with the unicellular green alga culture of the present technology leads to appropriate adjustment of expression time and sustained period of the advantageous effects of the present technology, as will be described in Examples below.

Laminarin, which is contained in brown algae, such as sea tangle, is linear polysaccharide composed of a glucose main chain having β1-3 bonds and β1-6 bonds, where the ratio of the β1-3 bonds to β1-6 bonds is usually approximately 3:1. The laminarin is also called laminin, β-glucan, or β1,3-glucan. The laminarin may be of commercially available one.

It is preferred that one or two or more selected from the group consisting of a *Geminella* extract, an *Uronema* extract, a *Chlorococcum* extract, and a *Chloroidium* extract, which is fast-acting compared to laminarin, is used in combination with laminarin or a brown alga extract containing laminarin.

The culture of the present technology can be effective for any disease and any pathogenic germ. In examples described below, expression of the PR-1a gene as an indicator of acquisition of plant resistance improved in *Arabidopsis thaliana* belonging to Brassicaceae. The culture of the present technology can be effective for any disease and any pathogenic germ. In examples described below, expression of the PR-1a gene as an indicator of acquisition of plant resistance improved in *Arabidopsis thaliana* belonging to Brassicaceae. The method of preventing or eliminating a plant disease according to the present technology is preferably carried out for prevention or elimination of plant disease by infection with pathogenic filamentous fungi.

Examples of the target pathogenic filamentous fungi include filamentous fungi leading to blue mold, leaf sheath rot, trunk rot, pink disease caused by filamentous fungi or rust fungi, rust, gray mold, bacterial shoot blight, yellow patch, fsarium wilt, verticillium wilt, powdery moldew, violet powdery mildew, ring rot, gray leaf spot, angular leaf spot, brown rot caused by filamentous fungi, leaf spot, leaf spot, Curvularia leaf spot, brown leaf spot, brown shot hole, bacterial palea browning, brown spot, and foot rot. More preferred are filamentous fungi belonging to genus *Colletotrichum*, especially *Colletotrichum higginsianum* (hereinafter, *C. higginsianum*). Examples of the bacterial disease include black rot, bacterial soft rot, and bacterial spot.

The present technology can be applied to a variety of plants including land plants and aquatic plants. Examples of the land plant include angiosperms and gymnosperms. Typical examples of the angiosperm include plants of Asteraceae, Orchidaceae, Liliaceae, Fabaceae, Poaceae, Rubiaceae, Euphorbiaceae, Cyperaceae, Apiaceae, Lamiaceae, Cucurbitaceae, Solanaceae, and Brassicaceae. The present technology is especially applicable to plants of Solanaceae and Brassicaceae. The technology is eminently suitable for plants that acquire resistance by the SAR model (for example, see NPL 1).

An example of the Liliaceae plants in broad sense is onion (genus *Allium*). An example of the Fabaceae plants is soybean.

An example of the Apiaceae plants in broad sense is carrot. Examples of the Poaceae plants include rice, Indian corn, and barley.

Examples of the Cucurbitaceae plants include melon, watermelon, winter melon, cucumber, and pumpkin. Examples of the Solanaceae plants include the tobacco, tomato, potato, eggplant, and green pepper.

Examples of the Brassicaceae plants include *Capsella bursa-pastoris* (nazuna), canola, cabbage, kale, Chinese cabbage, turnip, Japanese radish, wasabi, and mustard greens.

Since *Arabidopsis thaliana* of genus Brassicaceae exhibits improved expression of the PR-1a gene. which is an indicator of disease resistance, as described in Examples below, the culture of the present technology is preferably applied to the Brassicaceae plants.

The present technology can be applied to prevention of plant disease caused by pathogenic germs in any way.

The present technology can be applied to every portion of a plant, for example, aerial parts, such as leaves and stems, and underground parts, such as roots and roots stems.

Since the culture of the present technology contains polysaccharide, it should preferably be applied to underground parts in view of use of compost and persistence of the effect. Alternatively, the culture should preferably be applied to areal parts in view of a reduction in usage for cost saving.

The present technology can be used like common agricultural chemicals, for example, by spraying, infusion, coating, or burying. The preparation or the composition can be used as agricultural chemicals for plants or as materials to be compounded in agricultural chemicals or compost.

The culture of the present technology may be exposed to target plants in use. The use of the culture in such a way can induce disease resistance in the target plants.

The culture of the present technology can be exposed to the target plants in any manner. For example, a drug solution containing an effective level of active component is prepared, and then is sprayed onto plants. Alternatively, the solution is soaked into gauze, and then the gauze is put into contact with plants. In another embodiment, the solution is injected into stems of plants with syringes. In an alternative embodiment, the solution is infused to root of plants with droppers.

Drugs and compositions of the culture of the present technology can be prepared through any known process that is employed in production of conventional plant resistance inducers.

Any known solvent may be used that can dissolve the culture of the present technology in an effective concentration as an active ingredient. Preferred are solvents that are nontoxic or less toxic to plants. The culture of the present technology preferably is used in the form of aqueous dispersion or solution because water is common safe solvent.

The culture of the present technology may be used in any concentration as long as the culture can function as an active ingredient. The culture of the present technology may be used for any period. The culture of the present technology, which is primarily composed of polysaccharide carbohydrate, less affects plants themselves, environments, users, and animals even and is spontaneously decomposed into food components for plants if used in large quantities.

The culture of the present technology may be continuously used for long periods. Since the culture exert a maximum effect approximately five to eight days after its application, it is preferred that the culture be continuously used for at least three days, more preferably at least five days.

The concentration of the culture of the present technology may be determined by, for example, a method of inducing pest resistance in a plant, as will be described in Examples below. The lower limit of the concentration is preferably 0.01 mg/L, more preferably 0.1 mg/L, most preferably 1 mg/L in view of sufficient effects. The upper limit of the concentration is preferably 10 g/L, more preferably 5 g/L, most preferably 1 g/L in view of cost saving. The concentration accordingly ranges from preferably 0.02 mg/L to 10 g/L, more preferably 0.2 mg/L to 5 g/L.

The present technology provides the following configurations:

[1] A PR1 gene expression activator, a plant defense activator, or a plant disease preventive or ameliorating agent that contain a culture as an active ingredient of a unicellular alga containing a green photosynthetic pigment.

[2] A culture of a unicellular alga containing a green photosynthetic pigment for PR1 gene expression induction activation, plant resistance induction, or plant disease prevention or amelioration and use thereof.

[3] A method of activation of PR1 gene expression induction, inducing plant resistance, or preventing or ameliorating a plant from disease using a culture as an active ingredient of a unicellular alga containing a green photosynthetic pigment.

[4] Use of a culture of a unicellular alga containing a green photosynthetic pigment PR1 for producing a gene expression activator, a plant defense activator, or a plant disease preventive or ameliorating agent.

[5] In any one of [1] to [4], preferred is combined use of the culture of a unicellular alga containing a green photosynthetic pigment with a sea alga extract or laminarin.

[6] In any one of [1] to [5], the alga polysaccharide in the culture preferably contains at least uronic acid, more preferably contains 5 to 40 mass % uronic acid.

[7] In any one of [1] to [6], the alga polysaccharide in the culture preferably contains uronic acid and a neutral saccharide. More preferably the neutral saccharide is at least one selected from the group consisting of mannose, galactose. and rhamnose.

[8] In any one of [1] to [7], the alga is preferably an alga of class Trebouxiophyceae and/or an alga of class Chlorophyceae (green alga.

[9] In any one of [1] to [8], the alga is preferably at least one selected from the group consisting of genera *Euglena, Uronema, Chlorococcum, Geminella, Chloroidium* and *Chlorella* algae, more preferably at least one selected from the group consisting of genera *Geminella, Uronema, Chlorococcum*, and *Chloroidium* algae.

It is more preferred to use at least one selected from the group consisting of *Geminella* extract, *Uronema* extract, *Chlorococcum* extract, and *Chloroidium* extract, which has instantaneous effects compared to laminarin.

[10] In any one of [1] to [9], the alga preferably contains at least one selected from the group consisting of:

(a) *Uronema* being Chlorophyceae *Uronema* sp. (NBRC 113204), (b) *Chlorococcum* being Chlorophyceae *Chlorococcum* sp. (NBRC 113206).

(c) *Geminella* being Trebouxiophyceae *Geminella* sp. (NBRC 113205). and (d) *Chloroidium* being Trebouxiophyceae *Chloroidium saccharophilum* YAMA(NBRC 113207) and/or Trebouxiophyceae *Chloroidium saccharophilum* KAMI (NBRC 113807).

[11] In any one of [1] to [10], the alga is preferably at least one selected from the group consisting of [1] a Chlorophyceae *Uronema* sp. (NBRC 113204) alga strain; [2] a Trebouxiophyceae *Geminella* sp. (NBRC 113205) alga strain; [3] a Chlorophyceae *Chlorococcum* sp. (NBRC 113206) alga strain; [4] a Trebouxiophyceae *Chloroidium saccharophilum* YAMA (NBRC 113207) alga strain; and [5] a Trebouxiophyceae *Chloroidium saccharophilum* KAMI (NBRC 113807) alga strain.

[12] A method of producing a plant resistance inducing component, a PR1 gene expression inducing component, or a plant disease prevention or amelioration agent, containing cultivating a unicellular alga containing a green photosynthetic pigment under an aerobic condition, preferably in an autotrophic culture medium cultivation to yield a culture containing an extracellular polysaccharide.

[13] A unicellular alga containing a green photosynthetic pigment for production of a plant resistance inducing component, a PR1 gene expression inducing component, or a plant disease prevention or amelioration agent component, or use thereof.

[14] According to [12] or [13], the alga contains an alga of class Chlorophyceae and/or an alga of class Trebouxiophyceae.

[15] In any one of [12] to [14], the alga preferably contains at least one selected from the group consisting of *Euglena, Uronema, Chlorococcum, Geminella, Chloroidium,* and *Chlorella* algae, more preferably selected from the group consisting of *Uronema, Chlorococcum, Geminella,* and *Chloroidium* algae.

[16] In any one of [12] to [15], the alga preferably contains at least one selected from the group consisting of:

(a) *Uronema* being Chlorophyceae *Uronema* sp. (NBRC 113204).

(b) *Chlorococcum* being Chlorophyceae *Chlorococcum* sp. (NBRC 113206), (c) *Geminella* being Trebouxiophyceae *Geminella* sp. (NBRC 113205), and (d) *Chloroidium* being Trebouxiophyceae *Chloroidium saccharophilum* YAMA(NBRC 113207) and/or Trebouxiophyceae *Chloroidium saccharophilum* KAMI (NBRC 113807).

[17] In any one of [12] to [15], the alga contains at least one selected from the group consisting of (1) a Chlorophyceae *Uronema* sp. (NBRC 113204) alga strain; (2) a Trebouxiophyceae *Geminella* sp. (NBRC 113205) alga strain; (3) a Chlorophyceae *Chlorococcum* sp. (NBRC 113206) alga strain; (4) a Trebouxiophyceae *Chloroidium saccharophilum* YAMA (NBRC 113207) alga strain; and (5) a Trebouxiophyceae *Chloroidium saccharophilum* KAMI (NBRC 113807) alga strain.

[18] In any one of [12] to [17], the cultivation temperature preferably ranges from 5 to 40° C.

[19] In any one of [12] to [18], the cultivation pH preferably ranges from 1.5 to 10. [20] In any one of [12] to [19], the algae are preferably removed by centrifugal separation and/or filtration after the cultivation.

[21] In any one of [12] to [20], the culture is preferably lyophilized and then dissolved in water, and a water-soluble fraction is recovered after elimination of the alga.

[22] In any one of [12] to [21], the algae culture, preferably polysaccharide is prepared by a method of producing an alga culture preferably a polysaccharide.

EXAMPLES

The present technology will now be described in detail by way of examples that should not limit the technology.

Algae Strains Used

*Uronema* alga strain, *Chlorococcum* alga strain, *Geminella* alga strain, *Chloroidium* YAMA alga strain, and *Chloroidium* KAMI alga strain used were available from the NBRC Culture Collection (See Table 1). The respective 18srRNAs are also listed in Table 2 to 5 (SEQ ID NOs: 1-4) and Table 12 (SEQ ID NO: 5).

1) Chlorophyceae *Uronema* sp. (NBRC 113204): (Disclosed on Mar. 29, 2018/Web-site URL: www.nbrc.nite.go.jp, the Web-site printed on Mar. 29, 2018)

2) Chlorophyceae *Chlorococcum* sp. (NBRC 113206); (Disclosed on Mar. 29, 2018/Web-site URL: www.nbrc.nite-.go.jp, the Web-site printed on Mar. 29, 2018)

3) Trebouxiophyceae *Geminella* sp. (NBRC 113205): (Disclosed on Mar. 29, 2018/Web-site URL: www.nbrc.nite.go.jp, the Web-site printed on Mar. 29, 2018)

4) Trebouxiophyceae *Chloroidium saccharophilum* YAMA (NBRC 113207): (Disclosed on Mar. 29, 2018/Web-site URL: www.nbrc.nite.go.jp, the Web-site printed on Mar. 29, 2018)

TABLE 1

Table 1

| Alga strain | NBRC registration | Collected site | Date of colle | Source of separation | Source of separati | Isolation | Cultivation | Name of cultur | Results of Blast |
|---|---|---|---|---|---|---|---|---|---|
| Chlorophyceae *Uronema* sp. (NBRC 113204) | 2018 Jan. 26 | Chosei-gun, Chiba | 2013 Jul. 21 | Water | Tap water | Colony picking method | Passage: Slant | BG11 (pH 9.0) | emb\|FN824393.1\| *Uronema confervicola* partial 18S rRNA gene, c . . . 3151 0.0 emb\|FR717536.1\| *Uronema* sp. CCAP 335/1B genomic DNA containin . . . 3148 0.0 gb\|KM020180.1\| *Uronema minutum* strain SAG 386-1 18S ribosomal . . . 3124 0.0 |
| Chlorophyceae *Chlorococcum* sp. (NBRC 113206) | 2018 Jan. 26 | Tokiwa, Ohmachi-shi, Nagano | 2014 Sep. 1 | Water | Natural fresh water (in greenhouse) | Colony picking method | Passage: Slant | AF6 | gb\|M63001.1\|CAUUGEAC *Characium vacuolatum* 18S ribosomal RNA gene 2650 0.0 gb\|KM020023.1\| *Chlorococcum* sp. SAG 2467 18S ribosomal RNA ge . . . 2637 0.0 emb\|FR865591.1\| *Chlorococcum* sp. CCAP 11/52 genomic DNA conta . . . 2637 0.0 |

TABLE 1-continued

Table 1

| Alga strain | NBRC registration | Collected site | Date of colle | Source of separation | Source of separati | Isolation | Cultivation | Name of cultur | Results of Blast |
|---|---|---|---|---|---|---|---|---|---|
| Trebouxiophyceae *Geminella* sp. (NBRC 113205) | 2018 Jan. 26 | Tokiwa, Ohmachi-shi, Nagano | 2014 Sep. 1 | Water | Natural fresh water (in greenhouse) | Colony picking method | Passage: Slant | AF6 | gb\|EU434025.1\| *Geminella* sp. SAG 20.84 18S ribosomal RNA gene . . . 3119 0.0<br>gb\|EU434021.1\| *Geminella interrupta* strain SAG 8.91 18S ribos . . . 3032 0.0<br>gb\|EU434031.1\| *Stichococcus mirabilis* strain SAG 379-3a 18S r . . . 3029 0.0 |
| Trebouxiophyceae *Chloroidium saccharophilum* (NBRC 113207) | 2018 Jan. 26 | Lake Yamanaka, Yamanashi | Unknown | Water | Tap water | Colony picking method | Passage: Slant | Hot spring BG11 (pH 9.0) | gb\|KJ756839.1\| *Chloroidium saccharophilum* strain CCAP 211/27 . . . 3068 0.0<br>gb\|JQ315768.1\| *Chloroidium saccharophilum* strain KMMCC 195 18 . . . 3043 0.0<br>gb\|JQ315770.1\| *Chloroidium saccharophilum* strain KMMCC 158 18 . . . 2816 0.0 |

TABLE 2

```
Chlorophyceae Uronema sp. (NBRC 113204)
SEQ. ID. 1: 18srRNA gene, Base length: : 1750
TAGTCATATGCTTGTCTCAAAGATTAAGCCATGCATGTCTAAGTATAAATTGCTTATACTATGAAACTGCGAATGGCTCATTAAATCAGTTGT AGTTTATTTGATGATACCTTTCTACTCGGATAACCGTAGTAATTCTAGAGCTAATACGTGCGCAACTCCCGACTTCTGGAAGGGACGTGGTTA TTAGATCTAAGGCCAACCGGGCTTTGCCCGACCTGAGGTGAATCATTGTAACTCCACGAATCGCATGGCCTCGCGCCGGCGATGTTTCATTCA AACTTCTGCCCTATCAACTTTCGATGGTAGGATAGAGGCCTACCATGGTGGTAACGGGTGACGGAGGATTAGGGTTCGATTCCGGAGAGGGAG CCTGAGAAACGGCTACCACATCCAAGGAAGGCAGCAGGCGCGCAAATTACCCAATCCCGACACGGGGAGGTAGTGACAATAAATAACAATACC GGGCATTCAATGTCTGGTAATTGGAATGAGTACAATCTAAATCCCTTAACGAGTATCCATTGGAGGGCAAGTCTGGTGCCAGCAGCCGCGGTA ATTCCAGCTCCAATAGCGTATATTTAAGTTGTTGCAGTTAAAAAGCTCGTAGTTGGATTTCGGGTGGCTGTCTCGGTCCGCCTTACGGTGTG CACTGCTGTCGGCCACCTTTCTGTCGGGGACGGGCTCCTGGGCTTCACTGTCCGGGACTCGGAGTCGGCGAGGTTACTTTGAGTAAATTAGAG TGTTCAAAGCAAGCCTGAGCTCTGAATACATTAGCATGGAATAACATGATAGGACTCTGCCTATCTTGTTGGTCTGTAGGACCGGAGTAATG ATTAAGAGGGACAGTCGGGGGCATTCGTATTTCATTGTCAGAGGTGAAATTCTTGGATTTATGAAAGACGAACTTCTGCGAAAGCATTTGCCA AGTATGTCTTCATTAATCAAGAACGAAAGTTGGGGGCTCGAAGACGATTAGATACCGTCGTAGTCTCAACCATAAACGATGCCGACTAGGGAT CGGTGGGAGTTTTTTCGATGACTCCGTGGGCACCTTATGAGAAATCAAAGTCTTTGGGTTCCGGGGGGAGTATGGTCGCAAGGCTGAAACTTA AAGGAATTGACGGAAGGGCACCACCAGGCGTGGAGCCTGCGCTTAATTTGACTCAACACGGGAAACTTACCAGGTCCAGACATAGTGAGGA TTGACAGATTGAGAGCTCTTTCTTGATTCTATGGGTGGTGGTGCATGGCCGTTCTTAGTTGGTGGGTTGCCTTGTCAGGTTGATTCCGGTAAC GAACGAGACCTCAGCCTGCTAAATAGTCACTGCCGCTTTTTGCGGTTGGCAGACTTCTTAGAGGGACTATTGTCGTTTAGGCAATGGAAGTAT GAGGCAATAACAGGTCTGTGATGCCCTTAGATGTTCTGGGCCGCACGCGCGCTACACTGACGCATTCAACGAGCCTATCCTTGGCCGAGAGGC CCGGGTAATCTTTGAAACTGCGTCGTGATGGGGATAGATTATTGCAATTATTAGTCTTCAACGAGGAATGCCTAGTAAGCGCGAGTCATCAGC TCGCGTTGATTACGTCCCTGCCCTTTGTACACACCGCCCGTCGCTCCTACCGATTGGGTGTGCTGGTGAAGCGCTCGGATCGGGGCGGTCGG

GAGTCTCTCCCACCGTTCCTGAGAAGTCCGTTAAACCCTCCCACCTAGAGGAAGGAGAAGTCGTAACAAGGTTTCC
```

TABLE 3

```
Chlorophyceae Chlorococcum sp. (NBRC 113206)
SEQ. ID. 2: 18srRNA gene, Sequence length: 1743
TAGTCATATGCTTGTCTCAAAGATTAAGCCATGCATGTCTAAGTATAAACTGCTTATACGGTGAAACTGCGAATGGCTCATTAAATCAGTTAT AGTTTATTTGATGGTACCTTTACTCGGATAACCGTAGTAATTCTAGAGCTAATACGTGCGTAAATCCCGACTTATGGAAGGGACGTATTTATT AGATAAAAGGCCAGCCGGGCTTGCCCGACCCTAGGCGAATCATGATAACTTCACGAATCGCATGCCCTCGTGGCGGCGATGTTTCATTCAAAT TTCTGCCCTATCAACTTTCGATGGTAGGATAGAGGCCTACCATGGTGGTAACGGGTACGGAGGATTAGGGTTCGATTCCGGAGAGGGAGCCTG AGAAACGGCTACCACATCCAAGGAAGGCAGCAGGCGCGCAAATTACCCAATCCCGACACGGGGAGGTAGTGACAATAAATAACAATACTGGGC
```

TABLE 3-continued

ATTTATGTCTGGTAATTGGAATGAGTACAATGTAAATATCTTAACGAGTATCCATTGGAGGGCAAGTCTGGTGCCAGCAGCCGCGGTAATTCC
AGCTCCAATAGCGTATATTTAAGTTGTTGCAGTTAAAAAGCTCGTAGTTGGATTTCGGATGTGTTGTCGCGGTCTGCCTCTGGTATGTACTGC
GTTCGATGCATCTTTCTGCTGGGGACGAGCTCCTGGGCTTAACTGTCCGGGACTCGGAATCAGCGAAGTGACCTTGAGCAAACAAGAGTGTTC
AAAGCAAGCCTACGCTCTGAATTTTTTAGCATGGAATCACACGATAGGACTCTGGCCTATCTTGTTGGTCTGTAGGACCGGAGTAATGATTAA
GAGGGACAGTCGGGGGCATTCGTATTTCATTGTCAGAGGTGAAATTCTTGGATTTATGAAAGACGAACTTCTGCSAAAGCATTTGCCAAGGAT
GTTTTCATTGATCAAGAACGAAAGTTGGGGGCTCGAAGACGATTAGATACCGTCGTAGTCTCAACCATAAACGATGCCGACTAGGGATTGGCA
GGTGTTCAATTGATGACCCTGCCAGCACCTTATGAGAAATCAAAGTTTTTGGGTTCCGGGGGAGTATGGTCGCAAGGCTGAAACTTAAAGGA
ATTGACGGAAGGGCACCACCAGGCGTGGAGCCTGCGGCTTAATTTGACTCAACACGGGGAAACTTACCAGGTCCAGACACGGGGAGGATTGAC
AGATTGAGAGCTCTTTCTTGATTCTRTGGGTGGTGGTGCATGGCCGTTCTTAGTTGGTGGAGTGATTTGTCTGGTTAATTCCGTTAACGAACG
AGACCCCCGCCTGCTAACTAGTACCGGAAATGCTTAGCATTGCCGGCGACTTCTTAGAGGGACTTTCGGTGGTTAGCCGAAGGAAGATGGGGG
CAATAACAGGTCTGTGATGCCCTTAGATGTCCTGGGCCGCACGCGCGCTACACTGATGCGTTCAACGAGTTTATAACCTTGTCCGGCAGGACT
GGGTAATCTTGAAACGCGCATCGTGATAGGGATAGATTCTTGCAACTATTGATCTTGAACGAGGAATTCCTAGTAAACGCGAGTCATCAGCTC
GCATTGATTACGTCCCTGCCCTTTGTACACACCGCCCGTCGCACCTACCGATTGAACGATTCGGTGAAGCTTTCGGACCGCGCCGTTGGCTTC
TAGCCGGCGATGCGGGAAGTTATCTAAACCTCATCGTTTAGAGGAAGGTGAAGTCGTAACAAGGTTTCC

TABLE 4

Trebouxiophyceae Geminella sp. (NBRC 113205)
SEQ. ID. 3: 18srRNA gene, Base length: 1749
TAGTCATATGCTTGTCTCAAAGATTAAGCCATGCATGTCTAAGTATAAACTGCTTTATACGGTGAAACTGCGAATGGCTCATTAAATCAGTTA
TAGTTTATTTGATGGTATACTTACTCGGATACCCGTAGTAATTCTAGAGCTAATACGTGCGTACAGCCCGACTTCTGGAAGGGCCGCATATAT
TAGATTCAAGGCCAGCCGGGCTCTGCCCGCCTCGCGGTGAGTCATGATATTTTCACGAATCGCATGGCCTCGTGCCGGCGATGTTTCATTCAA
ATTTCTGCCCTATCAACTTTCGATGGTAGGATAGAGGCCTACCATGGTGGTAACGGGTGACGGAGGATTAGGGTTCGATTCCGGAGAGGGAGC
CTGAGAAACGGCTACCACATCCAAGGAAGGCAGCAGGCGCGCAAATTACCCAATCCTGATTCAGGGAGGTAGTGACAATAAATAACAATACCG
GGCTTTTCAAGTCTGGTAATTGGAATGAGTACAATCTAAACCCCTTAACGAGGATCCATTGGAGGGCAAGTCTGGTGCCAGCAGCCGCGGTAA
TTCCAGCTCCAATAGCGTATATTTAAGTTGTTGCAGTTAAAAAGCTCGTAGTTGGATTTCGGGTGGGGTGTGCCGGTCCGCCGTTTCGGTGTG
CACTGGCCCGTCCCATCTTGTTGGCGGGGACGGGCTCCTGGGCTTCACTGTCCGGGACCCGGAGTCGCCGAGGCTACTTTGAGTAAATTAGAG
TGTTCAAAGCAGGCAACCGCTCTGAATATTTCAGCATGGGATAGCATGATAGGACTCTGGTCCATCTTGCTGGTCTGTGGCACCGGAGTAATG
ATTAAGAGGGACAGTCGGGGGCATTCGTATTTCATTGTCAGAGGTGAAATTCTTGGATTTATGAAAGACGAACTTCTGCAAAGCATTTGCCA
AGGATGTTTTCATTAATCAAGAACGAAAGTTGGGGGCTCGAAGACGATTAGATACCGTCCTAGTCTCAACCATAAACGATGCCGACTAGGGAT
TGGCGGATGTTTCTTCGATGACTCCGCCAGCACCTTATGAGAAATCAAAGTTTTTGGGTTCCGGGGGGAGTATGGTCGCAAGGCTGAAACTTA
AAGGAATTGACGGAAGGGCACCACCAGGCGTGGAGCCTGCGGCTTAATTTGACTCAACACGGGGAAACTTACCAGGTCCAGACATAGTGAGGA
TTGACAGATTGAGAGCTCTTTCTTGATTCTATGGGTGGTGGTGCATGGCCGTTCTTAGTTGGTGGGTTGCCTTGTCAGGTTGATTCCGGTAAC
GAACGAGACCTCCGCCTGCTAACTAGTCACGGTTGGTTCTCCAGCCGGCGGACTTCTTAGAGGGACTATTGGCGATTAGCCAGTGGAAGTTGG
AGGCAATAACAGGTCTGTGATGCCCTTAGATGTTCTGGGCCGCACGCGCGCTACACTGATGCAATCAACGAGCCTATCCTTGGCCGGCAGGTC
CGGGTAATCTTGTAAACTGCATCGTGATGGGGATAGATTATTGCAATTATTAATCTTCAACGAGGAATGCCTAGTAAGCGCGATTCATCAGAT
CGCGTTGATTACGTCCCTGCCCTTTGTACACACCGCCCGTCGCTCCTACCGATTGGATGTGCTGGTGAAGTGTTCGGATCGGCGGCTGGGGGC
GGTTTCGCCACCAGCTGCTGAGAAGTTCATTAAACCCTCCCATCTAGAGGAAGGAGAAGTCGTAACAAGGTTTCC

TABLE 5

Trebouxiophyceae Chloroidium saccharophilum (NBRC 113207)
SEQ. ID. 4: 18srRNA gene, Base length: 3280

```
TAGTCATATGCTTGTCTCAAAGATTAAGCCATGCATGTCTAAGTATAAACTGCTTATACTGTGAAACTGCGAATGGCTCATTAAATCAGTTAT
AGTTTATTTGATGGTACCTACTACTCGGATAACCGTAGTAATTCTAGAGCTAATACGTGCGTAAATCCCGACTCCTGGAAGGGACGTATTTAT
TAGATAAAAGGCCGACCGGACTCCGTCCGACTCGCGGTGAATCATGATAACTTCACGAATCGCATGGCCTCGTGCCGGCGATGTTTCATTCAA
ATTTCTGCCCTATCAACTTTCGATGGTAGGATAGAGGCCTACCATGGTTTTGACGGGTGACGGAGGATTAGGGTTCGATTCCGGAGAGGGAGC
CTGAGAAACGGCTACCACATCCAAGGAAGGCAGCAGGCGCGCAAATTACCCAATCCCGACACGGGGAGGTAGTGACAATAAATAACAATACCG
GGCTTTTTCAAGTCTGGTAATTGGAATGAGTACAATCTAAATCCCTTAACGAGGATCAATTGGAGGGCAAGTCTGGTGCCAGCAGCCGCGGTA
ATTCCAGCTCCAATAGCGTATATTTAAGTTGTTGCAGTTAAAAAGCTCGTAGTTGGATTTCGGGCGGGGCCTGCCGGTCCGCCTCTGGTGTGC
ACTGGCATGGGCTCGCCTCGCTGTCGGGGACGGGCTCCTGGGCTTAACTGTCCGGGACTCGGAGTCGACGAGGTTACTTTGAGTAAATTAGAG
TGTTCAAAGCAGGCCTACGCTCTGAATACGTTAGCATGGAATAACACGATAGGACTCTGGCCTATCTTGTTGGTCTGTGGGACCGGAGTAATG
ATTAAGAGGGACGGTCGGGGGCATTCGTATTTCATTGTCAGAGGTGAAATTCTTGGATTTATGAAAGACGAACTTCTGCGAAAGCATTTGCCA
AGGATGTTTTCATTAATCAAGAACGAAAGTTGGGGGCTCGAAGACGATTAGATACCGTCCTAGTCTCAACCATAAACGATGCCGACTAGGGAT
CGGCGGGTGTTCTTTCGATGACCCCGCCGGCACCTTACGAGAAATCAAAGTTTTTGGGTTCCGGGGGGAGTATGGTCGCAAGGCTGAAACTTA
AAGGAATTGACGGAAGGGCACCACCAGGCGTTTGAATTGCTCTAGCGCCTAAAAGTCGATGATCAAACTTCGGCTAGTGGTGGGTTCTGATGG
ACCTGCTGCGACACTGTCAAATTGCGGGGACTTCCTAAAGCTCTCGGTGCCAAGCTGTAGTGGAAACGTTACAGTGGCCAAGGTTAACAGCCT
TGGGTAAGGCAACAACTCGAGAGATGCACCAATGGATGATCCGCAGCCAACTCCTAAGGATCTACAAACAAGGTCTATGGAAAAGGTTCACA
GACTAAATGACAGTGGGTACACTTAGAGTACGAACTCCAGTCTAGCCATGCGGTGCTTGACGACATTTTTTAGGCAATACACTCTCAGGTCTA
AGCAACGTCTATAGGCCACGGGCACGCACTCGGGGTCGTGGGGGCAGGCGCTGAAAGTCTCGCCACACTTGCTGCACTGGATGGTGCCCACGC
ACCGCTGCCGCTTGTTGTTGCCCTCCTGGGACTCGATGATGACATGCCCGCGCCTCCAGCAAAAAGGGGATATGATGCACAGGTGGGAGGCAG
TGTAGTCCTTGGACTTGCCTCCCTCAGGCAGATCCCTGCAAAGCTAGAGATGGGTGCAATCCCTTTCGTTTTAAGGCAACCACCGCCGACAAC
TCCACCTTGAGAGTAAATTCTCGGTTGGATTTCTCGGCCGCCGTTAGAAACATGGGAGAAGGGTGTAGCCCACCTGAAGTGTGCCAGCATGTG
TCGTACTGGACGGCTGTGAAGTTCTCCTTAGCCCAAATCAGGGCAGACAGCTGGTGCAGGTAGATCTGGCAGTTGGTGATGGGCCCAGGGGCA
ACCGTAGGTTCCCTTGGACACGCTGACCTTGCTGAGAGGGTACCTGCACGGTTGAAATGAGAACTCACTACTGTGACGTTCAAACTCACTATT
TCCACGACATTCGTTAACTCGCAACACACTCACCTCTCATTTGAGTTGCTGCTCCAGATCTGGCAAACTTTCCTCGCTGCTCCATCCTCAACT
TTGACTTGACCAGCTCTCTTGACGAGCGTCTCGTAGATGTACGTCATACAGTCAAAACTGAGTATGGCAACGTGCTGGAATGACATCTTGCCG
TTCCTCTTCGGTCCTTCAACGATAGACCTCTTCCCTGGCGATGCTTCGGGATGGGTGGCTCGATGACACTGGGCTCGCGAGGGGGACTGGCG
AAGTGCGTGCCGAGGTGCGCGTCCGAGAAGTCGGCGATCCTCTTCACTGGAGAAGACATCTTGGGTAGTGTGTTGCGTCCGAGTGAGCGAGAA
TGATTCGCTGCGAAGTTATTTCGAGGCGGCGCACGCCAGGCTGTTCGTACATTCTTGGAAATCTCTTGGAATGTCCGAAAGTTGCGCCGCCGC
ATGTAGATAGCAACGCTAGCGGTGGAATTGTACTTAAGATATAGTCGGCCCCCAGCCGAGAGGTTGGCTTATCGGAGGAAAGTCTTTCGAGAC
TGGAGAGTCGGTAAGGAGGTCGGTCAACATGCTCGTTCGTGGAGCGTTGTTGGTCGCCTTGGATCAGCGGGAGCCTGCGGCTTAATTTGACTC
AACACGGGAAAACTTACCAGGTCCAGACATAGTGAGGATTGACAGATTGAGAGCTCTTTCTTGATTCTATGGGTGGTGGTGCATGGCCGTTCT
TAGTTGGTGGGTTGCCCTTGTCAGGTTGATTCCGGTAACGAACGAGACCTCAGCCTGCTAAATAGTCACGCTCGGCTTCTGCCGGGCGGCAGCG
CTTCTTAGAGGGACTATCGGCGACTAGCCGATGGAAGTGTGAGGCAATAACAGGTCTGTGATGCCCTTAGATGTTCTGGGCCGCACGCGCGCT
ACACTGACGCAATCAACGAGCCCAGCCTTGGTCGAGAGACCCGGGTAATCTTGTAACCTGCGTCGTGATGGGCTAGACTCTTGCAATTATTA
GTCTTCAACGAGGAATGCCTAGTAAGCGCGAGTCATCAGCTCSCGTTGATTACGTCCCTGCCCTTTGTACACACCGCCCGTCGCTCCTACCGA
TTGGATGTGCTGGTGAAGCCCTAGGACTGGCGGCCTTTGGTGGTTCTCCGCCGACGGTCGCCGGGAATTCGGTTAAACCCTCCCATCTAGAGG
AAGGAGAAGTCGTAACAAGGTCTCC
```

Production Examples 1 to 4: Method of Producing Cultures (Cultures Containing Polysaccharides) Derived from Algae and Analysis Thereof <Method of Producing Cultures (Cultures Containing Polysaccharides) Derived from Algae>

Production Example 1

The slant medium (50 mL) containing "*Uronema* alga strain" listed in Table 1 and 6 was added to a minimum essential medium (100 mL) listed in Table 7 or 8 in a 300-mL Erlenmeyer flask, and the mixture was then preincubated under autotrophic cultivation conditions at an illuminance of 1500 to 10000 lux at 23° C. and 120 rpm for 12 days. The number of the alga cells may be preliminarily increased prior to the preincubation.

A culture solution 1 L after the preliminary incubation was then transferred into a 10-L jar fermentor, and was incubated for 12 days, which was referred to as Culture Solution 1 after incubation. The incubation was conducted under aerobic autotrophic cultivation conditions at an illuminance of 1500 to 10000 lux at 23° C., 200 rpm, and an aeration volume of 0.56 vvm.

Production Examples 2 to 4

"*Chlorococcum* alga strain", "*Geminella* alga strain", "*Chloroidium* alga strain" listed in Table 1 and 6 were each incubated as in the method of producing polysaccharides of the "*Uronema* alga strain" (see Table 1) to give Culture Solutions 2, 3, and 4, respectively.

An AF6 medium was used for incubation of *Chlorococcum* alga strain, *Geminella* alga strain, *Chlorella* alga strain, and *Euglena* alga strain (Table 7). A BG11 medium was used for incubation of *Uronema* alga strain and *Chloroidium* alga strain (Table 8).

<Recovery of Cultures 1 to 4 Derived from Algae in Production Examples 1 to 4>

Solution 1 derived from *Uronema* was centrifuged (7000 rpm (6500G), 25° C.) to separate the solution into supernatant fluid containing extracellular polysaccharides and alga bodies.

The supernatant fluid was then concentrated to 400 mL through an UF membrane having a molecular weight cut-off of 5000 and freeze-dried to give Culture 1 containing polysaccharides derived from *Uronema*.

Cultures 2 to 4 containing the polysaccharides listed in Table 6 were prepared from Solutions 2 to 4 derived from the respective alga strains (*Chlorococcum*, *Geminella*, and *Chloroidium*) as in the method of preparing Culture 1 derived from *Uronema*.

The yield of polysaccharides (mg/ culture supernatant 1 L) for each alga strain was determined by phenol-sulfuric acid colorimetry (authentic sample: glucose) using the supernatant fluid separated from alga bodies. The results are listed in Table 6.

TABLE 6

Table 6

| Genus of alga | Strain | Yield of Polysaccharide Concentration in Supernatant [mg/L] |
|---|---|---|
| *Uronema* | Chlorophyceae *Uronema* sp. (NBRC 113204) | 27.6 |
| *Chlorococcum* | Chlorophyceae *Chlorococcum* sp. (NBRC 113206) | 100.8 |
| *Geminella* | Trebouxiophyceae *Geminella* sp. (NBRC 113205) | 25.3 |
| *Chloroidium* | Trebouxiophyceae *Chloroidium saccharophilum* (NBRC 113207) | 313.6 |

TABLE 7

Table 7: Composition of AF6 culture medium

| Sodium nitrate | 14 mg |
|---|---|
| Ammonium nitrate | 2.2 mg |
| Magnesium sulfate hexahydrate | 3 mg |
| Calcium chloride dihydrate | 1 mg |
| Potassium dihydrogen phosphate | 1 mg |
| Dipotassium hydrogen phosphate | 0.5 mg |
| Iron citrate | 0.2 mg |
| Citric acid | 0.2 mg |
| Biotin | 0.2 µg |
| Thiamine hydrochloride | 1 µg |
| Vitamin B6 | 0.1 µg |
| Vitamin B12 | 0.1 µg |
| MES buffer | 40 mg |
| Trace metals | 0.5 mL |
| Distilled water | 99.8 mL |
| pH | 6.6 |
| Total volume | 100 mL |

TABLE 8

Table 8: Composition of BG11 culture medium

| Sodium nitrate | 150 mg |
|---|---|
| Dipotassium hydrogen phosphate | 4 mg |
| Magnesium sulfate hexahydrate | 7.5 mg |
| Calcium chloride dihydrate | 3.6 mg |
| Citric acid | 0.6 mg |
| Iron ammonium citrate | 0.6 mg |
| Sodium EDTA | 0.1 mg |
| Sodium carbonate | 2 mg |
| Trace metals | 0.1 mL |
| Distilled water | 99.9 mL |
| pH | 9 |
| Total volume | 100 mL |

<Analysis of Cultures Derived from Alga Strains in Production Examples 1 to 4>

Cultures 1 to 4 derived from the alga strains were each freeze-dried to give powder samples. Culture 1 was derived from *Uronema*, Culture 2 from *Chlorococcum*, Culture 3 from *Geminella*, and Culture 4 from *Chloroidium*.

Each powder sample was decomposed by acid hydrolysis (e.g., hydrolysis conditions: 72% sulfuric acid aqueous solution was added, stirred for one hour at a room temperature, and adjusted to 4% sulfuric acid aqueous solution, which was then autoclaved (121° C., one hour)). The contents of constituent neutral monosaccharides: mannose, arabinose, galactose. xylose, glucose, rhamnose, ribose, and fucose in the cultures were determined by HPLC and other means for sugar analysis. The contents of the monosaccharides in polysaccharides contained in the cultures derived from the alga strains are listed in Table 9.

1) Chlorophyceae *Uronema* sp. (NBRC 113204) alga strain: The culture derived from *Uronema* contained 25 mass % neutral monosaccharides, the main constituents of which were 13 mass % rhamnose and 5.5 mass % glucose.

2) Chlorophyceae *Chlorococcum* sp. (NBRC 113206) alga strain: The culture derived from *Chlorococcum* contained 71 mass % neutral monosaccharides, the main constituents of which were 20 mass % mannose, 23 mass % arabinose, and 24 mass % galactose.

3) Trebouxiophyceae *Geminella* sp. (NBRC 113205) alga strain: The culture derived from *Geminella* (first sample) contained 41 mass % neutral monosaccharides, the main constituents of which were 7 mass % arabinose, 13 mass % galactose, and 15 mass % rhamnose.

The culture derived from *Geminella* (second sample) contained 25 mass % neutral monosaccharides, the main constituents of which were 10 mass % mannose, 4 mass % galactose, 3 mass % rhamnose, and 3 mass % fucose.

4) Trebouxiophyceae *Chloroidium saccharophilum* (NBRC 113207) alga strain: The culture derived from *Chloroidium* contained 34 mass % neutral monosaccharides, the main constituents of which were 8 mass % mannose, 7 mass % arabinose, and 11 mass % galactose.

PR-1a gene promoter. Culture 1 was derived from the *Uronema*, Culture 2 from the *Chlorococcum*, Culture 3 from the *Geminella*, and Culture 4 from the *Chloroidium*.

The samples from Cultures 1 to 4 prepared with sterile water after germination were each added to a well at a volume ratio of 1:10 (final concentration). The final concentration in each plate was set at 0.02 wt % (200 pg/mL) in Plate 1 (Example 1) and 0.002 wt % (20 pg/mL) in Plate 2 (Example 2). Powdered culture samples were each diluted with sterile water into a 1% solution (10 mg/mL) which was then stored at −20° C.

Experiments were repeated 12 times for each sample treatment and induction of PR-1a promoter expression was assessed using Fluc luminescence activity as an index. The luminescent intensity after the plant treatment was defined as activity inducing the gene expression, the intensity of which was monitored over time.

The luminescent intensity of each well was measured with a photon counter GaAsP IMAGE INTENSIFIER UNIT C8600 (Hamamatsu Photonics K.K.) and analytical software Wasabi. The activity inducing PR-1a gene expression in each sample was assessed using the amount of expression of a reporter or F-luc calculated from the corresponding luminescent intensity.

TABLE 9

Table 9

| Genus of alga | Strain | Saccharides contents in sample (mass %) | | | | | | | | |
|---|---|---|---|---|---|---|---|---|---|---|
| | | Mannose | Arabinose | Galactose | Xylose | Glucose | Lamunose | Ribose | Fucose | Miscellaneous |
| *Uronema* | Chlorophyceae *Uronema* sp. (NBRC 113204) | 2.9 | 1.2 | 1.4 | 1.2 | 5.5 | 12.7 | 0.0 | 0.0 | 75.1 |
| *Chlorococcum* | Chlorophyceae *Chlorococcum* sp. (NBRC 113206) | 20.0 | 23.4 | 24.1 | 2.6 | 0.0 | 1.2 | 0.0 | 0.0 | 28.7 |
| *Geminella* | Trebouxiophyceae *Geminella* sp. (NBRC 113205) | 1.7 | 6.6 | 13.4 | 2.1 | 0.0 | 14.7 | 0.0 | 2.8 | 58.7 |
| *Chloroidium* | Trebouxiophyceae *Chloroidium saccharophilum* (NBRC 113207) | 8.4 | 7.2 | 10.8 | 5.0 | 0.0 | 2.6 | 0.0 | 0.0 | 66.0 |

Examples 1 to 2: Experiment Inducing the Expression of PR-1a Gene Promoter

*Arabidopsis thaliana* with introduction of a plasmid construct (PR-1a::Fluc$^+$) linked with a firefly luciferase gene downstream of a PR-1a gene promoter was seeded with sterile water of 100 μL on a 96-well plate. After a 5-day vernalization treatment, 0.1 mM (final concentration) of luciferin was added to the seeds and placed in a biotron (12 hours under light conditions, 12 hours under dark conditions, and 100% relative humidity).

The present examples can be carried out with reference to PLs 1 and 2, and NPL 1. A plasmid having a fusion gene (PR-1a::F-luc) linked with the firefly luciferase (F-luc) gene downstream of a Pathogenesis-related gene 1a (PR-1a) promoter derived from tobacco can be prepared based on NPL 1. The plasmid can be introduced into *Arabidopsis thaliana* via *Agrobacterium* (*Agrobacterium tumefaciens* LBA4404) to give transgenic *Arabidopsis thaliana* seeds (PR-1a::F-luc) having PR-1a::F-luc.

Cultures 1 to 4 derived from the alga strains were used as samples for the experiment inducing the expression of The time points for analysis in the consecutive monitoring were set at 0, 24, 48, 72, 96, 120, 144, 168, 192, and 216 hours. The relative value was defined as the relative luminescent intensity when a luminescent intensity at 0 hour was defined as 1. The results up to 120 hours are listed in Tables 10 and 11.

Tables 10 and 11 demonstrate that cultures containing the polysaccharides extracellularly produced in the algae have a remarkable activity inducing PR-1a gene expression. The cultures containing the polysaccharides are produced from *Uronema, Chlorococcum, Geminella*, and *Chloroidium*. The cultures are also produced from Chlorophyceae alga and/or Trebouxiophyceae alga.

Accordingly, the polysaccharides extracellularly produced by the unicellular algae having green photosynthetic dyes mainly increase the activity inducing PR-1a gene expression. These cultures are common in that they contain at least one neutral monosaccharide selected from the group consisting of mannose, rhamnose, and galactose, which probably involve in a certain effect.

The polysaccharide derived from *Uronema* contains a neutral monosaccharide comprising primarily of rhamnose and glucose. The polysaccharide containing these monosaccharides is probably involved in activation of PR-1a gene expression induction.

The polysaccharide derived from *Chlorococcum* contains a neutral monosaccharide comprising primarily of galactose, arabinose, and mannose. The polysaccharide containing these monosaccharides is probably involved in activation of PR-1a gene expression induction.

The polysaccharide derived from *Geminella* contains a neutral monosaccharide comprising primarily of mannose, rhamnose, and galactose. The polysaccharide containing these monosaccharides is probably involved in activation of PR-1a gene expression induction.

The polysaccharide derived from *Chloroidium* contains a neutral monosaccharide comprising primarily of galactose, mannose, arabinose, and xylose. The polysaccharide containing these monosaccharides is probably involved in activation of PR-1a gene expression induction.

TABLE 10

Table 10: PR1 gene expression activation [Relative luminescence]

| | Added amount 0.2 mg/mL | Time[h] | | | | |
|---|---|---|---|---|---|---|
| Genus of alaga | Strain | 0 | 18 | 24 | 48 | 72 |
| Uronema | Chlorophyceae Uronema sp. (NBRC 113204) | 1 | 2.015113 | 2.837538 | 2.569625 | 4.687945 |
| Chlorococcum | Chlorophyceae Chlorococcum sp. (NBRC 113206) | 1 | 2.150755 | 2.66728 | 3.527722 | 13.83039 |
| Geminella | Trebouxiophyceae Geminella sp. (NBRC 113205) | 1 | 2.135826 | 3.407769 | 11.51535 | 30.25197 |
| Chloroidium | Trebouxiophyceae Chloroidium saccharophilum (NBRC 113207) | 1 | 1.931512 | 2.910375 | 4.28351 | 10.95094 |
| H₂O | | 1 | 2.04478 | 3.170034 | 3.242729 | 3.232298 |

| | Time[h] | | | | | |
|---|---|---|---|---|---|---|
| Genus of alaga | 96 | 120 | 144 | 168 | 192 | 216 |
| Uronema | 29.8431 | 45.83574 | <u>63.20372</u> | 45.84708 | 27.86021 | 11.87001 |
| Chlorococcum | 50.50659 | <u>52.91926</u> | 39.51581 | 22.13991 | 19.29159 | 9.766256 |
| Geminella | 66.08334 | <u>82.84546</u> | 76.7754 | 50.92574 | 34.16851 | 14.50444 |
| Chloroidium | 33.45235 | 33.48607 | <u>44.93943</u> | 42.02884 | 35.70795 | 18.29983 |
| H₂O | 3.816372 | 4.060429 | 5.17002 | 8.541311 | <u>10.03633</u> | 4.471838 |

[Relative luminescence: Underlines indicate maximum values.]

TABLE 11

Table 11: PR1 gene expression activation [Relative luminescence]

| | Added amount 0.02 mg/mL | Time[h] | | | | |
|---|---|---|---|---|---|---|
| Genus of alga | Strain | 0 | 18 | 24 | 48 | 72 |
| Uronema | Chlorophyceae Uronema sp. (NBRC 113204) | 1 | 2.344906 | 2.350257 | 2.876471 | 5.374137 |
| Chlorococcum | Chlorophyceae Chlorococcum sp. (NBRC 113206) | 1 | 2.213412 | 1.917782 | 3.817816 | 18.64823 |
| Geminella | Trebouxiophyceae Geminella sp. (NBRC 113205) | 1 | 2.876112 | 2.651426 | 4.199231 | 14.74126 |
| Chloroidium | Trebouxiophyceae Chloroidium saccharophilum (NBRC 113207) | 1 | 2.297243 | 2.553308 | 2.700599 | 4.173792 |
| H₂O | | 1 | 2.543387 | 2.560874 | 2.845528 | 3.872533 |

| | Time[h] | | | | | |
|---|---|---|---|---|---|---|
| Genus of alga | 96 | 120 | 144 | 168 | 192 | 216 |
| Uronema | 16.17612 | <u>32.38847</u> | 30.03042 | 25.98359 | 18.29701 | 9.487009 |
| Chlorococcum | <u>54.55558</u> | 49.81676 | 32.97586 | 20.3836 | 15.75056 | 9.601393 |
| Geminella | 36.62572 | 51.72981 | <u>52.42426</u> | 39.84524 | 26.07605 | 12.34956 |
| Chloroidium | 16.83339 | <u>27.58056</u> | 27.24056 | 26.4352 | 20.73234 | 11.19997 |
| H₂O | 5.427904 | 4.818676 | 6.523825 | 9.718492 | 11.19932 | <u>12.91869</u> |

[Relative luminescence: Underlines indicate maximum values.]

Examples 3 to 4: Bioactivity Testing

<Alga Strains Used in Examples 3 to 4>

The *Uronema* alga strain used in Example 3 was Chlorophyceae *Uronema* sp. (NBRC 113204) alga strain.

The *Chlorococcum* alga strain used in Example 3 was Chlorophyceae *Chlorococcum* sp. (NBRC 113206) alga strain.

The *Geminella* alga strain used in Example 3 was Trebouxiophyceae *Geminella* sp. (NBRC 113205) alga strain.

Trebouxiophyceae *Chloroidium saccharophilum* KAMI (NBRC 113807) alga strain was available from the NBRC Culture Collection (See Table 1). a 18srRNA of which is disclosed in Table 12 (SEQ ID NO: 5). The *Chlorococcum* KAMI alga strain used in Example 3 was Trebouxiophyceae *Chloroidium saccharophilum* KAMI (NBRC 113807) alga strain.

*Euglena* alga strain sampled from Katanuma in Naruko. Osaki city, Miyagi prefecture, Japan in May, 2005 was used in Example 3.

Laminarin (made by Sigma-Aldrich) was used as a positive control in Example 3.

The *Chlorococcum* alga strain used in Example 4 was Chlorophyceae *Chlorococcum* sp. (NBRC 113206) alga strain.

The *Chlorella* alga strain used in Example 4 was *Chlorella vulgaris* Chikugo strain (Chikugo strain: *Chlorella* Industry Co., Ltd.).

5) Trebouxiophyceae *Chloroidium saccharophilum* KAMI (NBRC 113807): (Disclosed on Feb. 25, 2019/Website URL: www.nbrc.nite.go.jp, the Web-site printed on Feb. 25, 2019). The strain was sampled on May 7, 2012 at Kaminoko Pond (origin of the strain), Shari-gun, Kiyosato-cho, Hokkaido.

TABLE 12

```
Trebouxiophyceae Chloroidium saccharophilum (NBRC 113807)
SEQ. ID. 5: 18srRNA gene, Base length: 3280
CTGGTTGATCCTGCCAGTAGTCATATGCTTGTCTCAAAGATTAAGCCATGCATGTCTAAGTATAAACTGCTTATACTGTGAAACTGCGAATGG CTCATTAAATCAGTTATAGTTTATTTGATGGTACCTACTACTCGGATAACCGTAAACGAGAGTTATTGCGGTAGGGAGACGAGAGTCGTCCCT AGTGGCTCGTCAGAGCTGCGACACTGTCAAATTGCCTGGACATCCCGCTACGCTGAGGAGACCGTCTGATTGGGGAAACCTGATCGGACACCG ACGGTGAAAGCCGTCGGGTATGGTAACACTTCCTCGGCTAGGGACTATGGGCAGCCAAGCTCTAAAAGCCTCCTTGGCTCAAGAGTGCAGTTC ACAGACTAAATGGCAGTGGGTGTCCGCCTCCCCAGGCGGATGCTTAAGATATAGTCGGTCCCCATCGAGAGGTGGACCGTCGGAGGAATGGGG CGTTCAGCCCCAGGAGAGCCGATGGTGTCTGACGACTGGAGTCGCCAGGCGGAGCAAACGAGTAATTCTAGAGCTAATACGTGCGTAAATCCC GACTCCTGGAAGGGACGTATTTATTAGATAAAAGGCCGACCGGACTCCGTCCGACTCGCGGTGAATCATGATAACTTCACGAATCGCATGGCC TTGTGCCGGCGATGTTTCATTCAAATTTCTGCCCTATCAACTTTCGATGGTAGGATAGAGGCCTACCATGGTTTTGACGGGTGACGGAGGATT AGGGTTCGATTCCGGAGAGGGAGCCTGAGAAACGGCTACCACATCCAAGGAAGGCAGCAGGCGCGCAAATTACCCAATCCCGACACGGGGAGG TAGTGACAATAAATAACAATACCGGGCTTTTTCAAGTCTGGTAATTGGAATGAGTACAATCTAAATCCCTTAACGAGGATCAATTGGAGGGCA AGTCTGGTGCCAGCAGCCGCGGTAATTCCAGCTCCAATAGCGTATATTTAAGTTGTTGCAGTTAAAAAGCTCGTAGTTGGATTTCGGGCGGGG CCTGCCGGTCCGCCTCTGGTGTGCACTGGCATGGGCTCGCCTCGCTGTCGGGGACGGGCTCCTGGGCTTAACTGTCCGGGACTCGGAGTCGAC GAGGTTACTTTGAGTAAATTAGAGTGTTCAAAGCAGGCCTACGCTCTGAATACGTTAGCATGGAATAACACGATAGGACTCTGGCCTATCTTG TTGGTCTGTGGGACCGGAGTAATGATTAAGAGGGACGGTCGGGGGCATTCGTATTTCATTGTCAGAGGTGAAATTCTTGGATTTATGAAAGAC GAACTTCTGCGAAAGCATTTGCCAAGGATGTTTTCATTAATCAAGAACGAAAGTTGGGGGCTCGAAGACGATTAGATACCGTCCTAGTCTCAA CCATAAACGATGCCGACTAGGGATCGGCGGGTGTTCTTTCGATGACCCCGCCGGCACCTTACGAGAAATCAAAGTTTTTGGGTTCCGGGGGGA GTATGGTCGCAAGGCTGAAACTTAAAGGAATTGACGGAAGGGCACCACCAGGCGTTTGAATTGCTCTAGCGCCTAAAAGTCGGCCGTCAAACG CCGACTAGTGGCCGGTTCTCACGAGCCGTCTGCGACACTGCCAAATTGCGGGGACCTCCTAAAGCTCTCGGTGCCAAGCCTCAGTGGAAACGC TGCGGTGGCCAGGGTTAACAGCCCTGGGTACGGCAACAATCCGAGAGATGAACCAATGGACGATCCGCAGCCAACTCCTACCGAGCCGCCTGG CTCCATGGAAGAGGTTCACAGACTAAATGACAGTGGGTGCATCGAGAGATGTGCTTAAGATATAGTCGGCCCCCAGTCGAGAGGCTGGCCCGT CGGAGGAAGGACCTTTGTGGGTCTGGAGAGCCGTCGGGAGGGCGCTGGACGGCTTCGAGCCGCCTGGCCCCTTGGATCAGCGGGAGCCTGCG GCTTAATTTGACTCAACACGGGAAAACTTACCAGGTCCAGACATAGTGAGGATTGACAGATTGAGAGCTCTTTCTTGATTCTATGGGTGGTGG TGCATGGCCGTTCTTAGTTGGTGGGTTGCCTTGTCAGGTTGATTCCGGTAACGAACGAGACCTCAGCCTGCTAAATAGTCACGCTCGGCTTCT GCCGGGCGGCAGCGCTTCTTAGAGGGACTATCGGCGACTAGCCGATGGAAGTGTGAGGCAATAACAGGTCTGTGATGCCCTTAGATGTTCTGG GCCGCACGCGCGCTACACTGACGCAATCAACGAGCCCAGCCTTGGTCGAGAGACCCGGGTAATCTTGTAACCTGCGTCGTGATGGGCTAGAC TCTTGCAATTATTAGTCTTCAACGAGGAATGCCTAGTAAGCGCGAGTCATCAGCTCGCGTTGATTACGTCCCTGCCCTTTGTACACACCGCCC GTCGCTCCTACCGATTGGATGTGCTGGTGAAGCCCTAGGACTGGCGGCCTTTGGTGGTTCTCCGCCKACGGTCGCCGGGAATTCGGTTAAACC

CTCCCATCTAGAGGAAGGAGAAGTCGTAACAAGGTCTCCGTAGGTGAACCTGCGGAAGG
```

<Samples to be Used in Examples 3 to 4>

Culture samples from the alga strains listed in <Alga strains used in Examples 3 to 4> were prepared as in <Production Examples 1 to 4: Method of producing cultures (cultures containing polysaccharides) derived from algae and analysis thereof> and <Method of producing cultures (cultures containing polysaccharides) derived from algae>.

Specifically, an AF6 medium was used for incubation of the *Chlorococcum, Geminella, Chloroidium* YAMA, and *Chlorella* alga strains (Table 7). A BG11 medium was used for incubation of the *Uronema* and *Chloroidium* KAMI alga strains (Table 8). A KO2 medium was used for incubation of the *Euglena* alga strain. These alga strains were incubated under optimum conditions with reference to the Production Examples 1 to 4 to give cultures containing polysaccharides.

Accordingly, samples prepared in Example 3 were Culture 5 derived from *Uronema*, Culture 6 derived from *Chlorococcum*, Culture 7 derived from *Geminella*, Culture 8 derived from *Chloroidium* KAMI, Culture 9 derived from *Euglena*. Samples prepared in Example 4 were Culture 10 derived from *Chloroidium* YAMA and Culture 11 from *Chlorella*.

The yield of polysaccharides (mg/culture supernatant 1 L) of the *Chloroidium* KAMI alga strain was then determined by phenol-sulfuric acid colorimetry (authentic sample: glucose) using the supernatant fluid separated from the alga, the value of which was 300 mg/L.

[Composition of KO2 Medium]

Sodium nitrate 85 mg, ammonium sulfate 66 mg. potassium dihydrogen phosphate 27 mg, magnesium phosphate heptahydrate 25 mg, calcium chloride dihydrate 11 mg, iron sulfate heptahydrate 2 mg, EDTA-2Na 3 mg, N1 Metals solution *[1] 0.1 mL, and distilled water 99 mL. pH 2, volume of preparation 100 mL.

*[1] [Composition of N1 Metals solution]

Boric acid 2.86 g, manganese chloride tetrahydrate 1.81 g, zinc sulfate heptahydrate 0.22 g, copper sulfate pentahydrate 0.08 g, molybdenum trioxide 15 mg, and distilled water 1000 mL. Volume of preparation 1000 mL.

Examples 3 to 4: Experiments Inducing the Expression of PR-1a Gene Promoter

In the experiments inducing the expression of PR-1a gene promoter in Examples 3 to 4, the induction activity in each sample was assessed as in <Examples 1 to 2: Experiment inducing the expression of PR-1a gene promoter>. The concentration of each culture used was 0.02 mg/mL.

The time points set for analysis in the consecutive monitoring were 0, 24, 48, 72, 96, 120, 144, 168, 192, 216, 240, and 264 hours. The luminescent intensity was a relative value to the luminescent intensity defined as 1 at 0 hour.

The results of Example 3 are listed in Table 13 and FIG. 1, and the results of Example 4 in Table 14, in the experiments inducing the expression of PR-1a gene promoter.

Tables 13 and 14 demonstrate that cultures containing the polysaccharides extracellularly produced in the algae have a remarkable activity inducing PR-1a gene expression. The cultures containing the polysaccharides are produced from *Uronema, Chlorococcum, Geminella, Chloroidium* (preferably KAMI), *Euglena*, and *Chlorella*. The results demonstrate that the products can activate PR-1a gene expression induction.

The products derived from *Uronema* (1.35 times), *Chlorococcum* (1.11 times), *Geminella* (1.37 times), *Chloroidium* KAMI (1.12 times), and *Euglena* (1.10 times) each shows a higher peak value (activity) than that from Laminarin. Additionally, the time point at the peak value for each product was shifted ahead of that for Laminarin. The times to the respective peaks for the products are 0.67 to 0.78 times that for Laminarin, which demonstrates the products are fast-acting as compared with Laminarin. Although active ingredients in the cultures derived from the algae are still being studied, polysaccharides are generally slow-acting due to their high molecular weights. The cultures derived from the algae, which contain high-molecular-weight polysaccharides like Laminarin, are usually fast-acting. Such point is believed to be advantageous. The time of the action can also be easily adjusted if the products and Laminarin are used in combination of two or more.

TABLE 13

PR1 gene expression activation [Relative luminescence to laminarin]

| Alga genus | Strain | Added amount 0.02 mg/mL | | | | | | |
|---|---|---|---|---|---|---|---|---|
| | | | | | Time[h] | | | |
| | | 0 | 24 | 48 | 72 | 96 | 120 | 144 |
| Uronema | Chlorophyceae Uronema sp. (NBRC 113204) | 1 | 0.92072 | 2.05286 | 4.90871 | 15.5257 | 34.8459 | 48.8371 |
| Chlorococcum | Chlorophyceae Chlorococcum sp. (NBRC 113206) | 1 | 0.65032 | 2.17644 | 7.11482 | 19.0127 | 41.6991 | 44.5333 |
| Geminella | Trebouxiophyceae Geminella sp. (NBRC 113205) | 1 | 3.23037 | 7.46235 | 23.4769 | 41.0275 | 54.8255 | 55.0453 |
| Chloroidium | Trebouxiophyceae Chloroidium saccharophilum KAMI (NBRC 113807) | 1 | 1.73599 | 3.60535 | 7.59362 | 20.1718 | 42.308 | 44.7848 |
| Euglena | Euglena strain | 1 | 1.07117 | 6.15862 | 9.32706 | 9.25918 | 12.5741 | 20.0871 |
| Positive control | Laminarin | 1 | 0.90769 | 2.36507 | 4.82292 | 6.29698 | 11.5668 | 20.2688 |
| Negative control | H2O | 1 | 1.29104 | 7.24038 | 9.03144 | 6.63425 | 6.69066 | 9.82638 |

TABLE 13-continued

PR1 gene expression activation [Relative luminescence to laminarin]

|  | Time[h] | | | | |
| --- | --- | --- | --- | --- | --- |
| Alga genus | 168 | 192 | 216 | 240 | 264 |
| *Uronema* | <u>53.7513</u> | 48.2393 | 36.1757 | 22.3529 | 15.8256 |
| *Chlorococcum* | 34.9519 | 15.4237 | 7.717 | 4.75754 | 3.85307 |
| *Geminella* | 32.3748 | 13.5808 | 5.98286 | 3.18762 | 2.48524 |
| *Chloroidium* | 41.8631 | 28.4421 | 14.9399 | 7.29695 | 3.94352 |
| *Euglena* | 37.1346 | 43.095 | <u>43.9868</u> | 32.2371 | 19.0438 |
| Positive control | 36.3979 | 37.8044 | <u>39.9504</u> | 34.5435 | 25.4281 |
| Negative control | 16.8447 | 16.9865 | 15.5657 | <u>17.3962</u> | 15.7416 |

[Relative luminescence: Underlines indicate maximum values.]

TABLE 14

Table 14: PR1 gene expression activation [Relative luminescence]

| Alga | Strain | Added amount 0.02 mg/mL | Time[h] | | | | |
| --- | --- | --- | --- | --- | --- | --- | --- |
| | | 0 | 24 | 48 | 72 | 96 | 120 |
| Chlorella | Chikugo strain | 1 | 1.5368 | 3.421 | 6.0457 | 10.739 | 15.2 |
| Negative control | H2O | 1 | 1.291 | 7.2404 | 9.0314 | 6.6343 | 6.6907 |

| | | Time[h] | | | | | |
| --- | --- | --- | --- | --- | --- | --- | --- |
| | | 144 | 168 | 192 | 216 | 240 | 264 |
| Chlorella | Chikugo strain | 15.644 | 16.148 | 16.136 | <u>19.345</u> | 15.373 | 8.0254 |
| Negative control | H2O | 9.8264 | 16.845 | 16.987 | 15.566 | <u>17.396</u> | 15.742 |

[Relative luminescence: Underlines indicate maximum values.]

<Analysis of Cultures Derived from Alga Strains in Examples 3 to 4>

Cultures derived from the alga strains in Examples 3 to 4 were analyzed. In detail, the samples used in Example 3 were Culture 5 derived from *Uronema*, Culture 6 derived from *Chlorococcum*, Culture 7 derived from *Geminella*, and Culture 8 derived from *Chloroidium* KAMI. The sample used in Example 4 was Culture 10 derived from *Chloroidium* YAMA.

The cultures derived from the alga strains were each analyzed by an ABEE Labeling method (Yasuno, S., et al., Biosci. Biotechnol. Biochem., 61, 1944(1997), Yasuno, S., et al., Biosci. Biotechnol. Biochem., 63, 1353(1999)) on the following monosaccharides: Man (mannose), Ara (arabinose), Gal (galactose), Xyl (xylose), Glc (glucose), Rha (rhamnose), Rib (ribose), Fuc (fucose), NAc-GlcN (N-acetylglucosamine), NAc-GalN (N-acetylgalactosamine), NAc-ManN (N-acetylmannosamine), GalUA (galacturonic acid), and GlcUA (glucuronic acid).

1) HPLC

ACQUITY UPLC H Class System (manufactured by Waters)

ACQUITY UPLC BEH C18 Column, 1.7 µm, 2.1×100 mm (manufactured by J-Oil Mills, INC.). Column temperature: 50° C., Mobile phase: A/B=0.2 M potassium borate (pH 8.9)/ACN, flow rate: 0.7 mL/min, detection: fluorescence (excitation. 305 nm, Emission. 360 nm)

Milli-Q water was added to each sample to give a 10 mg/mL solution, 10 µL of which was prepared as a sample for hydrolysis. In detail, each sample was fractionated into 10 µL per tube. After trifluoroacetic acid (TFA) was added to the sample, the mixture was stirred, centrifuged, and heated for 3 hours at 100° C. After air cooling, the sample was centrifuged and dried with a SpeedVac. 2-Propanol was added to the sample, and the solution was stirred and dried using a SpeedVac. Pyridine/methanol and acetic anhydride were added to the sample, which was then allowed to react for 30 minutes at room temperature. The solution was dried using a SpeedVac for the subsequent ABEE labeling step. Reagents for the ABEE labeling (ABEE, sodium cyanoborohydride, acetic acid, and methanol) were added to the solution, which was then allowed to react for 1 hour at 80° C. The solution was post-treated with 200 µL MQW and 200 µL chloroform, the aqueous layer of which was collected and injected into HPLC. A calibration curve for each monosaccharide was created based on peak areas and the contents of the monosaccharides contained in the sample were determined.

The concentration of each sample was adjusted to 100 pg of dried culture for 1 mL of solution and the content of uronic acid in each culture was then determined by a carbazole sulfuric acid method (on the basis of GalUA). The content of uronic acid (on the basis of GalUA) in each sample is listed in Table 16.

TABLE 15

Table 15

| | | Contents of saccharides in sample (mass %) Proportion of monosaccharides | | | | | | |
|---|---|---|---|---|---|---|---|---|
| Genus of alga | Alga | Man 180.16 | Ara 150.13 | Gal 180.16 | Xyl 150.13 | Glc 180.16 | Rha 164.16 | Rib 150.13 |
| Uronema | Chlorophyceae Uronema sp. (NBRC 113204) | 4.0 | 0.0 | 1.1 | 1.0 | 0.9 | 8.8 | 0.0 |
| Chlorococcum | Chlorophyceae Chlorococcum sp. (NBRC 113206) | 14.5 | 23.5 | 17.7 | 4.6 | 0.0 | 0.5 | 0.0 |
| Geminella | Trebouxiophyceae Geminella sp. (NBRC 113205) | 21.4 | 0.0 | 3.8 | 0.0 | 0.5 | 2.3 | 0.0 |
| Chloroidium (KAMI) | Trebouxiophyceae Chloroidium saccharophilum KAMI (NBRC 113807) | 17.3 | 11.0 | 10.8 | 8.3 | 0.0 | 4.9 | 0.0 |
| Chloroidium (YAMA) | Trebouxiophyceae Chloroidium saccharophilum YAMA (NBRC 113207) | 10.5 | 0.0 | 10.5 | 0.0 | 4.4 | 0.0 | 0.0 |

| | Contents of saccharides in sample (mass %) Proportion of monosaccharides | | | | | | |
|---|---|---|---|---|---|---|---|
| Genus of alga | Fuc 164.16 | NAcGlcN 221.21 | NAcGalN 221.21 | NAcManN 221.21 | GalUA 194.14 | GlcUA 194.14 | Miscellaneous |
| Uronema | 0.9 | 0.6 | 0.0 | 0.0 | 0.0 | 9.6 | 73.0 |
| Chlorococcum | 0.0 | 0.9 | 0.0 | 0.0 | 0.0 | 14.1 | 24.2 |
| Geminella | 1.8 | 1.9 | 0.0 | 0.0 | 0.0 | 13.9 | 54.3 |
| Chloroidium (KAMI) | 0.0 | 1.0 | 0.0 | 0.0 | 0.0 | 10.8 | 35.9 |
| Chloroidium (YAMA) | 0.0 | 0.0 | 0.0 | 0.0 | 0.0 | 0.0 | 74.5 |

TABLE 16

Table 16: Uronic acid content in alga in sample (mass %)

| Genus of alga | Strain | Content [%] |
|---|---|---|
| Uronema | Chlorophyceae Uronema sp. (NBRC 113204) | 22.3 |
| Chlorococcum | Chlorophyceae Chlorococcum sp. (NBRC 113206) | 16.4 |
| Geminella | Trebouxiophyceae Geminella sp. (NBRC 113205) | 11.6 |
| Chloroidium (KAMI) | Trebouxiophyceae Chloroidium saccharophilum KAMI (NBRC 113807) | 21.8 |
| Chloroidium (YAMA) | Trebouxiophyceae Chloroidium saccharophilum YAMA (NBRC 113207) | 15.4 |

Content was determined by carbazole-sulfric acid method (Abs 530 nm): Std. GalUA Tables 15 and 16 show the analytical results of saccharides and uronic acid, respectively, by the ABEE labeling method.

Table 15 shows the proportion of monosaccharides in polysaccharides contained in each of the cultures derived from the *Geminella, Uronema, Chlorococcum*, and *Chloroidium* alga strains.

The polysaccharide derived from *Uronema* contains Rhamnose, mannose, and glucuronic acid as main constituent monosaccharides.

The polysaccharide derived from *Chlorococcum* contains mannose, arabinose, galactose, and glucuronic acid as main constituent monosaccharides.

The polysaccharide derived from *Geminella* contains mannose and glucuronic acid as main constituent monosaccharides.

The polysaccharide derived from *Chloroidium* KAMI contains mannose, arabinose, galactose, xylose, rhamnose, and glucuronic acid as main constituent monosaccharides.

The polysaccharide derived from *Chloroidium* YAMA contains mannose, galactose, and glucose as main constituent monosaccharides.

Polysaccharides contained in the cultures derived from the *Geminella, Uronema, Chlorococcum*, and *Chloroidium* alga strains contain uronic acid. Table 16 shows the content of uronic acid (on the basis of GalUA) in each sample. Since the polysaccharides extracellularly produced by the unicellular algae containing green photosynthetic dyes contain uronic acid, the polysaccharides probably exhibit activity inducing PR-1a gene expression (for example, high efficacy rate) which is different from that by Laminarin containing no uronic acid.

As described above, each polysaccharide contains uronic acid and neutral monosaccharides and is probably involved in activation of PR-1a gene expression induction.

It would appear that the cultures according to the present technology, which are produced by unicellular algae containing green photosynthetic dyes, exhibit no direct insecticidal or bactericidal effect. It would also appear that the cultures according to the present technology, which exhibit no direct insecticidal or bactericidal effect, can reduce the occurrence rate of resistant bacteria and the application rate, can exhibit the objective effect for a long term, and can less effect on organisms other than ones for pest control. The cultures according to the present technology contain abundant polysaccharides being carbon resources and a variety of constituents, and thus have potential effects as plant fertilizers.

The cultures according to the present technology, which are prepared by liquid cultivation, exhibit high solubility in water, and thus can be readily used in combination with irrigation water in farms. Insoluble components, if present, contained in the cultures according to the present technology will be gradually decomposed after application such as spraying, and the degradants would function as fertilizers for a long term with less environmental burden. A further advantage is low risk of internal exposure during application of the culture, unlike agrochemicals.

The cultures according to the present technology have broad utility since the cultures can be applied to any required crop at any required time and place.

The invention claimed is:

1. A method of inducing plant resistance comprising a step of applying to a plant a culture of a unicellular alga *Chlorococcum* sp. NBRC 113206 strain as an active ingredient for inducing plant resistance to pathogens, wherein
the culture comprises an extracellular polysaccharide containing 5 to 25 mass % uronic acid and at least one neutral monosaccharide selected from the group consisting of mannose, galactose, and rhamnose.

2. The method of inducing plant resistance according to claim t, wherein the culture has Pathogensis-Related Gene 1 (PR1) gene expression induction activity for PR1 gene expression induction.

3. The method of inducing plant resistance according to claim 1, wherein the culture is produced by cultivating the unicellular alga *Chlorococcum* sp. NBRC 113206 strain under an aerobic condition using sun light or artificial light.

4. The method of inducing plant resistance according to claim 1, wherein the culture has fast-acting Pathogensis-Related Gene 1 (PR1) gene expression induction activity for PR1 gene expression induction compared to that of laminarin.

* * * * *

SEQUENCE LISTING

```
<160> NUMBER OF SEQ ID NOS: 5

<210> SEQ ID NO 1
<211> LENGTH: 1750
<212> TYPE: DNA
<213> ORGANISM: Uronema sp. NBRC113204

<400> SEQUENCE: 1
tagtcatatg cttgtctcaa agattaagcc atgcatgtct aagtataaat tgcttatact      60
atgaaactgc gaatggctca ttaaatcagt tgtagtttat ttgatgatac ctttctactc     120
ggataaccgt agtaattcta gagctaatac gtgcgcaact cccgacttct ggaagggacg     180
tggttattag atctaaggcc aaccgggctt tgcccgacct gaggtgaatc attgtaactc     240
cacgaatcgc atggcctcgc gccggcgatg tttcattcaa acttctgccc tatcaacttt     300
cgatggtagg atagaggcct accatggtgg taacgggtga cggaggatta gggttcgatt     360
ccggagaggg agcctgagaa acggctacca catccaagga aggcagcagg cgcgcaaatt     420
acccaatccc gacacgggga ggtagtgaca ataaataaca ataccgggca ttcaatgtct     480
ggtaattgga atgagtacaa tctaaatccc ttaacgagta tccattggag ggcaagtctg     540
gtgccagcag ccgcggtaat tccagctcca atagcgtata tttaagttgt tgcagttaaa     600
aagctcgtag ttggatttcg ggtggctgtc tgcggtccgc cttacggtgt gcactgctgt     660
cggccacctt tctgtcgggg acgggctcct gggcttcact gtccgggact cggagtcggc     720
gaggttactt tgagtaaatt agagtgttca aagcaagcct gagctctgaa tacattagca     780
tggaataaca tgataggact ctggcctatc ttgttggtct gtaggaccgg agtaatgatt     840
aagagggaca gtcgggggca ttcgtatttc attgtcagag gtgaaattct tggatttatg     900
aaagacgaac ttctgcgaaa gcatttgcca agtatgtctt cattaatcaa gaacgaaagt     960
tgggggctcg aagacgatta gataccgtcg tagtctcaac cataaacgat gccgactagg    1020
gatcggtggg agtttttttcg atgactccgt gggcacctta tgagaaatca aagtctttgg   1080
gttccggggg gagtatggtc gcaaggctga aacttaaagg aattgacgga agggcaccac    1140
caggcgtgga gcctgcggct taatttgact caacacggga aaacttacca ggtccagaca    1200
tagtgaggat tgacagattg agagctcttt cttgattcta tgggtggtgg tgcatggccg    1260
ttcttagttg gtgggttgcc ttgtcaggtt gattccggta acgaacgaga cctcagcctg    1320
ctaaatagtc actgccgctt tttgcggttg gcagacttct tagagggact attgtcgttt    1380
aggcaatgga agtatgaggc aataacaggt ctgtgatgcc cttagatgtt ctgggccgca    1440
cgcgcgctac actgacgcat tcaacgagcc tatccttggc cgagaggccc gggtaatctt    1500
tgaaactgcg tcgtgatggg gatagattat tgcaattatt agtcttcaac gaggaatgcc    1560
tagtaagcgc gagtcatcag ctcgcgttga ttacgtccct gccctttgta cacaccgccc    1620
gtcgctccta ccgattgggt gtgctggtga agcgctcgga tcgggggcgg tcgggagtct    1680
```

```
ctcccaccgt tcctgagaag tccgttaaac cctcccacct agaggaagga gaagtcgtaa    1740
caaggtttcc                                                           1750

<210> SEQ ID NO 2
<211> LENGTH: 1743
<212> TYPE: DNA
<213> ORGANISM: Chlorococcum sp. NBRC113206

<400> SEQUENCE: 2
tagtcatatg cttgtctcaa agattaagcc atgcatgtct aagtataaac tgcttatacg      60
gtgaaactgc gaatggctca ttaaatcagt tatagtttat ttgatggtac ctttactcgg    120
ataaccgtag taattctaga gctaatacgt gcgtaaatcc cgacttatgg aagggacgta    180
tttattagat aaaaggccag ccgggcttgc ccgaccctag gcgaatcatg ataacttcac    240
gaatcgcatg ccctcgtggc ggcgatgttt cattcaaatt tctgccctat caactttcga    300
tggtaggata gaggcctacc atggtggtaa cgggtacgga ggattagggt tcgattccgg    360
agagggagcc tgagaaacgg ctaccacatc caaggaaggc agcaggcgcg caaattaccc    420
aatcccgaca cggggaggta gtgacaataa ataacaatac tgggcattta tgtctggtaa    480
ttggaatgag tacaatgtaa atatcttaac gagtatccat tggagggcaa gtctggtgcc    540
agcagccgcg gtaattccag ctccaatagc gtatatttaa gttgttgcag ttaaaaagct    600
cgtagttgga tttcggatgt gttgtcgcgg tctgcctctg gtatgtactg cgttcgatgc    660
atctttctgc tggggacgag ctcctgggct taactgtccg ggactcggaa tcagcgaagt    720
gaccttgagc aaacaagagt gttcaaagca agcctacgct ctgaattttt tagcatggaa    780
tcacacgata ggactctggc ctatcttgtt ggtctgtagg accggagtaa tgattaagag    840
ggacagtcgg gggcattcgt atttcattgt cagaggtgaa attcttggat ttatgaaaga    900
cgaacttctg cgaaagcatt tgccaaggat gttttcattg atcaagaacg aaagttgggg    960
gctcgaagac gattagatac cgtcgtagtc tcaaccataa acgatgccga ctagggattg   1020
gcaggtgttc aattgatgac cctgccagca ccttatgaga aatcaaagtt tttgggttcc   1080
ggggggagta tggtcgcaag gctgaaactt aaaggaattg acgaagggc accaccaggc    1140 gtggagcctg cggcttaatt tgactcaaca cggggaaact taccaggtcc agacacgggg   1200
aggattgaca gattgagagc tctttcttga ttctrtgggt ggtggtgcat ggccgttctt   1260
agttggtgga gtgatttgtc tggttaattc cgttaacgaa cgagaccccc gcctgctaac   1320
tagtaccgga aatgcttagc attgccggcg acttcttaga gggactttcg gtggttagcc   1380
gaaggaagat gggggcaata acaggtctgt gatgccctta gatgtcctgg ccgcacgcg    1440 cgctacactg atgcgttcaa cgagtttata accttgtccg gcaggactgg gtaatcttga   1500
aacgcgcatc gtgatagga tagattcttg caactattga tcttgaacga ggaattccta    1560
gtaaacgcga gtcatcagct cgcattgatt acgtccctgc cctttgtaca caccgcccgt   1620
cgcacctacc gattgaacga ttcggtgaag cttcggacc gcgccgttgg cttctagccg    1680
gcgatgcggg aagttatcta aacctcatcg tttagaggaa ggtgaagtcg taacaaggtt   1740
tcc                                                                  1743

<210> SEQ ID NO 3
<211> LENGTH: 1749
<212> TYPE: DNA
<213> ORGANISM: Geminella sp. NBRC113205
```

<400> SEQUENCE: 3

```
tagtcatatg cttgtctcaa agattaagcc atgcatgtct aagtataaac tgctttatac    60
ggtgaaactg cgaatggctc attaaatcag ttatagttta tttgatggta tacttactcg   120
gatacccgta gtaattctag agctaatacg tgcgtacagc ccgacttctg aagggccgc    180
atatattaga ttcaaggcca gccgggctct gcccgcctcg cggtgagtca tgatattttc   240
acgaatcgca tggcctcgtg ccggcgatgt ttcattcaaa tttctgccct atcaactttc   300
gatggtagga tagaggccta ccatggtggt aacgggtgac ggaggattag ggttcgattc   360
cggagaggga gcctgagaaa cggctaccac atccaaggaa ggcagcaggc gcgcaaatta   420
cccaatcctg attcagggag gtagtgacaa taaataacaa taccgggctt ttcaagtctg   480
gtaattggaa tgagtacaat ctaaaccccct aacgaggat ccattggagg gcaagtctgg   540
tgccagcagc cgcggtaatt ccagctccaa tagcgtatat ttaagttgtt gcagttaaaa   600
agctcgtagt tggatttcgg gtggggtgtg ccggtccgcc gtttcggtgt gcactggccc   660
gtcccatctt gttggcgggg acgggctcct gggcttcact gtccgggacc cggagtcgcc   720
gaggctactt tgagtaaatt agagtgttca aagcaggcaa ccgctctgaa tatttcagca   780
tgggatagca tgataggact ctggtccatc ttgctggtct gtggcaccgg agtaatgatt   840
aagagggaca gtcgggggca ttcgtatttc attgtcagag gtgaaattct tggatttatg   900
aaagacgaac ttctgcgaaa gcatttgcca aggatgtttt cattaatcaa gaacgaaagt   960
tgggggctcg aagacgatta gataccgtcc tagtctcaac cataaacgat gccgactagg  1020
gattggcgga tgtttcttcg atgactccgc cagcacctta tgagaaatca agttttttgg  1080
gttccggggg gagtatggtc gcaaggctga aacttaaagg aattgacgga agggcaccac  1140
caggcgtgga gcctgcggct taatttgact caacacgggg aaacttacca ggtccagaca  1200
tagtgaggat tgacagattg agagctcttt cttgattcta tgggtggtgg tgcatggccg  1260
ttcttagttg gtgggttgcc ttgtcaggtt gattccggta acgaacgaga cctccgcctg  1320
ctaactagtc acggttggtt ctccagccgg cggacttctt agagggacta ttggcgatta  1380
gccagtggaa gttggaggca ataacaggtc tgtgatgccc ttagatgttc tgggccgcac  1440
gcgcgctaca ctgatgcaat caacgagcct atccttggcc ggcaggtccg ggtaatcttg  1500
taaactgcat cgtgatgggg atagattatt gcaattatta atcttcaacg aggaatgcct  1560
agtaagcgcg attcatcaga tcgcgttgat tacgtccctg cccttttgtac acaccgcccg  1620
tcgctcctac cgattggatg tgctggtgaa gtgttcggat cggcggctgg gggcggtttc  1680
gccaccagct gctgagaagt tcattaaacc ctcccatcta gaggaaggag aagtcgtaac  1740
aaggtttcc                                                         1749
```

<210> SEQ ID NO 4
<211> LENGTH: 3280
<212> TYPE: DNA
<213> ORGANISM: Chloroidium saccharophilum NBRC113207

<400> SEQUENCE: 4

```
tagtcatatg cttgtctcaa agattaagcc atgcatgtct aagtataaac tgcttatact    60
gtgaaactgc gaatggctca ttaaatcagt tatagtttat tgatggtac ctactactcg   120
gataaccgta gtaattctag agctaatacg tgcgtaaatc ccgactcctg aagggacgt    180
atttattaga taaaaggccg accggactcc gtccgactcg cggtgaatca tgataacttc   240
acgaatcgca tggcctcgtg ccggcgatgt ttcattcaaa tttctgccct atcaactttc   300
```

```
gatggtagga tagaggccta ccatggtttt gacgggtgac ggaggattag ggttcgattc    360
cggagaggga gcctgagaaa cggctaccac atccaaggaa ggcagcaggc gcgcaaatta    420
cccaatcccg acacggggag gtagtgacaa taaataacaa taccgggctt tttcaagtct    480
ggtaattgga atgagtacaa tctaaatccc ttaacgagga tcaattggag ggcaagtctg    540
gtgccagcag ccgcggtaat tccagctcca atagcgtata tttaagttgt tgcagttaaa    600
aagctcgtag ttggatttcg ggcggggcct gccggtccgc ctctggtgtg cactggcatg    660
ggctcgcctc gctgtcgggg acgggctcct gggcttaact gtccgggact cggagtcgac    720
gaggttactt tgagtaaatt agagtgttca aagcaggcct acgctctgaa tacgttagca    780
tggaataaca cgataggact ctggcctatc ttgttggtct gtgggaccgg agtaatgatt    840
aagagggacg gtcgggggca ttcgtatttc attgtcagag gtgaaattct tggatttatg    900
aaagacgaac ttctgcgaaa gcatttgcca aggatgtttt cattaatcaa gaacgaaagt    960
tgggggctcg aagacgatta gataccgtcc tagtctcaac cataaacgat gccgactagg   1020
gatcggcggg tgttctttcg atgaccccgc cggcacctta cgagaaatca agttttttgg   1080
gttccggggg gagtatggtc gcaaggctga aacttaaagg aattgacgga agggcaccac   1140
caggcgtttg aattgctcta gcgcctaaaa gtcgatgatc aaacttcggc tagtggtggg   1200
ttctgatgga cctgctgcga cactgtcaaa ttgcggggac ttcctaaagc tctcggtgcc   1260
aagctgtagt ggaaacgtta cagtggccaa ggttaacagc cttgggtaag gcaacaactc   1320
gagagatgca ccaatggatg atccgcagcc aactcctaag gatctacaaa caaaggtcta   1380
tggaaaaggt tcacagacta aatgacagtg ggtacactta gagtacgaac tccagtctag   1440
ccatgcggtg cttgacgaca tttttaggc aatacactct caggtctaag caacgtctat    1500
aggccacggg cacgcactcg gggtcgtggg ggcaggcgct gaaagtctcg ccacacttgc   1560
tgcactggat ggtgcccacg caccgctgcc gcttgttgtt gccctcctgg gactcgatga   1620
tgacatgccc gcgcctccag caaaaagggg atatgatgca caggtgggag gcagtgtagt   1680
ccttggactt gcctccctca ggcagatccc tgcaaagcta gagatgggtg caatcccttt   1740
cgttttaagg caaccaccgc cgacaactcc accttgagag taaattctcg gttggatttc   1800
tcggccgccg ttagaaacat gggagaaggg tgtagcccac ctgaagtgtg ccagcatgtg   1860
tcgtactgga cggctgtgaa gttctcctta gcccaaatca gggcagacag ctggtgcagg   1920
tagatctggc agttggtgat gggcccaggg gcaaccgtag gttcccttgg acacgctgac   1980
cttgctgaga gggtacctgc acggttgaaa tgagaactca ctactgtgac gttcaaactc   2040
actatttcca cgacattcgt taactcgcaa cacactcacc tctcatttga gttgctgctc   2100
cagatctggc aaactttcct cgctgctcca tcctcaactt tgacttgacc agctctcttg   2160
acgagcgtct cgtagatgta cgtcatacag tcaaaactga gtatggcaac gtgctggaat   2220
gacatcttgc cgttcctctt cggtccttca acgatagacc tcttccctgg cgatgcttcg   2280
ggatggggtg gctcgatgac actgggctcg cgaggggggac tggcgaagtg cgtgccgagg   2340
tgcgcgtccg agaagtcggc gatcctcttc actggagaag acatcttggg tagtgtgttg   2400
cgtccgagtg agcgagaatg attcgctgcg aagttatttc gaggcggcgc acgccaggct   2460
gttcgtacat tcttggaaat ctcttggaat gtccgaaagt tgcgccgccg catgtagata   2520
gcaacgctag cggtggaatt gtacttaaga tatagtcggc ccccagccga gaggttggct   2580
tatcggagga aagtctttcg agactggaga gtcggtaagg aggtcggtca acatgctcgt   2640
```

-continued

| | |
|---|---|
| tcgtggagcg ttgttggtcg ccttggatca gcgggagcct gcggcttaat ttgactcaac | 2700 |
| acgggaaaac ttaccaggtc cagacatagt gaggattgac agattgagag ctctttcttg | 2760 |
| attctatggg tggtggtgca tggccgttct tagttggtgg gttgccttgt caggttgatt | 2820 |
| ccggtaacga acgagacctc agcctgctaa atagtcacgc tcggcttctg ccgggcggca | 2880 |
| gcgcttctta gagggactat cggcgactag ccgatggaag tgtgaggcaa taacaggtct | 2940 |
| gtgatgccct tagatgttct gggccgcacg cgcgctacac tgacgcaatc aacgagccca | 3000 |
| gccttggtcg agagacccgg gtaatcttgt aacctgcgtc gtgatggggc tagactcttg | 3060 |
| caattattag tcttcaacga ggaatgccta gtaagcgcga gtcatcagct cgcgttgatt | 3120 |
| acgtccctgc cctttgtaca caccgcccgt cgctcctacc gattggatgt gctggtgaag | 3180 |
| ccctaggact ggcggccttt ggtggttctc cgccgacggt cgccgggaat tcggttaaac | 3240 |
| cctcccatct agaggaagga gaagtcgtaa caaggtctcc | 3280 |

<210> SEQ ID NO 5
<211> LENGTH: 2570
<212> TYPE: DNA
<213> ORGANISM: Chloroidium saccharophilum NBRC11380

<400> SEQUENCE: 5

| | |
|---|---|
| ctggttgatc ctgccagtag tcatatgctt gtctcaaaga ttaagccatg catgtctaag | 60 |
| tataaactgc ttatactgtg aaactgcgaa tggctcatta atcagttat agtttatttg | 120 |
| atggtaccta ctactcggat aaccgtaaac gagagttatt gcggtaggga gacgagagtc | 180 |
| gtccctagtg gctcgtcaga gctgcgacac tgtcaaattg cctggacatc ccgctacgct | 240 |
| gaggagaccg tctgattggg gaaacctgat cggacaccga cggtgaaagc cgtcgggtat | 300 |
| ggtaacactt cctcggctag ggactatggg cagccaagct ctaaaagcct ccttggctca | 360 |
| agagtgcagt tcacagacta atggcagtg ggtgtccgcc tccccaggcg gatgcttaag | 420 |
| atatagtcgg tccccatcga gaggtggacc gtcggaggaa tggggcgttc agccccagga | 480 |
| gagccgatgg tgtctgacga ctggagtcgc caggcggagc aaacgagtaa ttctagagct | 540 |
| aatacgtgcg taaatcccga ctcctggaag ggacgtattt attagataaa aggccgaccg | 600 |
| gactccgtcc gactcgcggt gaatcatgat aacttcacga atcgcatggc cttgtgccgg | 660 |
| cgatgtttca ttcaaatttc tgccctatca actttcgatg gtaggataga ggcctaccat | 720 |
| ggttttgacg ggtgacggag gattagggtt cgattccgga gagggagcct gagaaacggc | 780 |
| taccacatcc aaggaaggca gcaggcgcgc aaattaccca atcccgacac ggggaggtag | 840 |
| tgacaataaa taacaatacc gggcttttc aagtctggta attggaatga gtacaatcta | 900 |
| aatcccttaa cgaggatcaa ttggagggca agtctggtgc cagcagccgc ggtaattcca | 960 |
| gctccaatag cgtatattta agttgttgca gttaaaaagc tcgtagttgg atttcgggcg | 1020 |
| gggcctgccg gtccgcctct ggtgtgcact ggcatgggct cgcctcgctg tcggggacgg | 1080 |
| gctcctgggc ttaactgtcc gggactcgga gtcgacgagg ttactttgag taaattagag | 1140 |
| tgttcaaagc aggcctacgc tctgaatacg ttagcatgga ataacacgat aggactctgg | 1200 |
| cctatcttgt tggtctgtgg gaccggagta atgattaaga gggacggtcg ggggcattcg | 1260 |
| tatttcattg tcagaggtga aattcttgga tttatgaaag acgaacttct gcgaaagcat | 1320 |
| ttgccaagga tgttttcatt aatcaagaac gaaagttggg ggctcgaaga cgattagata | 1380 |
| ccgtcctagt ctcaaccata aacgatgccg actaggatc ggcgggtgtt ctttcgatga | 1440 |
| ccccgccggc accttacgag aaatcaaagt ttttgggttc cggggggagt atggtcgcaa | 1500 |

```
ggctgaaact taaaggaatt gacggaaggg caccaccagg cgtttgaatt gctctagcgc    1560
ctaaaagtcg gccgtcaaac gccgactagt ggccggttct cacgagccgt ctgcgacact    1620
gccaaattgc ggggacctcc taaagctctc ggtgccaagc ctcagtggaa acgctgcggt    1680
ggccagggtt aacagccctg ggtacggcaa caatccgaga gatgaaccaa tggacgatcc    1740
gcagccaact cctaccgagc cgcctggctc catggaagag gttcacagac taaatgacag    1800
tgggtgcatc gagagatgtg cttaagatat agtcggcccc cagtcgagag gctggcccgt    1860
cggaggaagg acctttgtgg gtctggagag ccgtcgggga gggcgctgga cggcttcgag    1920
ccgcctggcc ccttggatca gcgggagcct gcggcttaat ttgactcaac acgggaaaac    1980
ttaccaggtc cagacatagt gaggattgac agattgagag ctctttcttg attctatggg    2040
tggtggtgca tggccgttct tagttggtgg gttgccttgt caggttgatt ccggtaacga    2100
acgagacctc agcctgctaa atagtcacgc tcggcttctg ccgggcggca gcgcttctta    2160
gagggactat cggcgactag ccgatggaag tgtgaggcaa taacaggtct gtgatgccct    2220
tagatgttct gggccgcacg cgcgctacac tgacgcaatc aacgagccca gccttggtcg    2280
agagacccgg gtaatcttgt aacctgcgtc gtgatgggc tagactcttg caattattag    2340
tcttcaacga ggaatgccta gtaagcgcga gtcatcagct cgcgttgatt acgtccctgc    2400
cctttgtaca caccgcccgt cgctcctacc gattggatgt gctggtgaag ccctaggact    2460
ggcggccttt ggtggttctc cgcckacggt cgccgggaat tcggttaaac cctcccatct    2520
agaggaagga gaagtcgtaa caaggtctcc gtaggtgaac ctgcggaagg              2570
```